(12) United States Patent
Yeh et al.

(10) Patent No.: US 9,777,300 B2
(45) Date of Patent: Oct. 3, 2017

(54) HYBRID ORGANIC-INORGANIC SYSTEM FOR PRODUCING BIOFUELS

(71) Applicant: The Regents of the University of California, Oakland, CA (US)

(72) Inventors: Yi-Chun Yeh, Emeryville, CA (US); Steven W. Singer, Berkeley, CA (US); Swapnil R. Chhabra, Oakland, CA (US); Harry R. Beller, Berkeley, CA (US); Jana Mueller, Mountain View, CA (US)

(73) Assignee: The Regents of the University of California, Oakland, CA (US)

( * ) Notice: Subject to any disclaimer, the term of this patent is extended or adjusted under 35 U.S.C. 154(b) by 48 days.

(21) Appl. No.: 14/273,371

(22) Filed: May 8, 2014

(65) Prior Publication Data
US 2014/0242649 A1    Aug. 28, 2014

Related U.S. Application Data

(63) Continuation of application No. PCT/US2012/064216, filed on Nov. 8, 2012.

(60) Provisional application No. 61/557,357, filed on Nov. 8, 2011.

(51) Int. Cl.
| | |
|---|---|
| C07K 16/28 | (2006.01) |
| C12P 7/64 | (2006.01) |
| C12P 5/00 | (2006.01) |
| C12P 5/02 | (2006.01) |
| C12P 7/02 | (2006.01) |
| C12P 7/62 | (2006.01) |
| C07K 1/13 | (2006.01) |
| C12N 1/38 | (2006.01) |
| C12P 7/16 | (2006.01) |
| C07K 14/245 | (2006.01) |

(52) U.S. Cl.
CPC .............. *C12P 7/6409* (2013.01); *C07K 1/13* (2013.01); *C07K 14/245* (2013.01); *C12N 1/38* (2013.01); *C12P 5/007* (2013.01); *C12P 5/02* (2013.01); *C12P 5/026* (2013.01); *C12P 7/02* (2013.01); *C12P 7/16* (2013.01); *C12P 7/62* (2013.01); *C12P 7/625* (2013.01); *Y02E 50/10* (2013.01)

(58) Field of Classification Search
CPC ........ C12Q 2563/159; B01J 2219/0072; B01J 2219/00743; C07K 16/28; G01N 33/582; G01N 33/588; G01N 21/6428; Y02E 50/10; Y10S 977/902
See application file for complete search history.

(56) References Cited

U.S. PATENT DOCUMENTS

2009/0191593 A1    7/2009   Burk et al.

FOREIGN PATENT DOCUMENTS

WO    2010046774 A1    4/2010

OTHER PUBLICATIONS

Basit, H., Sharma, K.S., Van Der Heyden, A., Gondran, C., Breyton, C., Dumy, P., Winnik, F.M., and Labbe, P., Chemical Communications, 2012, 48, 6037-6039.
Beller, H.R., et al, Genes Involved in Long-Chain Alkene Biosynthesis in Micrococcus luteus. Applied and Environmental Microbiology 2010, 76:1212-1223.
Berkane, E., Orlik, F., Stegmeier, F.K., Charbit, A., Winterhalter, M., and Benz, R., Biochemistry, 2006, 45, 2708-2720.
Carrico, I.S., Carlson, Bil., Bertozzi, C.R., Introducing genetically encoded aldehydes into proteins. Nature chemical biology 2007, 3:321-322.
Flayhan, A., Wien, F., Paternostre, M., Boulanger, P., and Breyton, C., Biochimie, 2012, 94, 1982-1989.
Fukui, T., Ohsawa, K., Mifune, J., Orita, I., and Nakamura, S., Applied Microbiology and Biotechnology, 2011, 89, 1527-1536.
Jose, J., Meyer, T.F.: The autodisplay story, from discovery to biotechnical and biomedical applications. Microbiol Mol Biol Rev 2007, 71:600-619.
Koebnik, R., Locher, K.P., Van Gelder, R., Molecular Microbiology, 2000, 37, 239-253.
Li, H., Opgenorth, P.H., Wernick, D.G., Rogers, S., Wu, T.Y., Higshide, W., Malati, P., Huo, Y.X., Cho, K.M., and Liao, J.C., Science, 2012, 335, 1596-1596.
Meyer, J.R., Dobias, D.T., Weitz, J.S., Barrick, J.E., Quick, R.T., and Lenski, R.E., Science, 2012, 335, 428-432.
Mondigler, M., Vogele, R.T., and Heller, K.J., Fems Microbiology Letters, 1995, 130, 293-300.
Mondigler, M., Holz, T., Heller, K.J.: Identification of the receptor-binding regions of pb5 proteins of bacteriophages T5 and BF23. Virology 1996, 219:19-28.
Plancon, L, Janmot, C., Le Maire, M., Desmadril, M., Bonhivers, L., Letellier, L., Boulanger, P.: Characterization of a high-affinity complex between the bacterial outer membrane protein FhuA and the phage T5 protein pb5. J Mol Biol 2002, 318:557-569.
Pohlmann, A., Fricke, W.F., Reinecke, F., Kusian, B., Liesegang, H., Cramm, R., Eitinger, T., Ewering, E., Poetter, M., Schwartz, E., et al: Genome sequence of the bioplastic-producing "Knallgas" host cell Ralstonia eutropha H16. Nat Biotechnol 2006, 24:1257-1262.
Pohlmann, A., Fricke, W.F., Reinecke, F., Kusian, B., Liesegang, H., Cramm, R., Eitinger, T., Ewering, C., Potter, M., Schwartz, E., Strittmatter, A., Voss, I., Gottschalk, G., Steinbuchel, A., Friedrich B., Bowien, B., Nature Biotechnology, 2007, 25, 478-478.

(Continued)

*Primary Examiner* — Kagnew H Gebreyesus
(74) *Attorney, Agent, or Firm* — Robin C. Chiang; Lawrence Berkeley National Laboratory

(57) ABSTRACT

The present invention provides for a system for converting $CO_2$ and $H_2$ to one or more biologically derived compounds. In some embodiments, the system comprises a host cell comprising one or more nucleic acids encoding genes for a recombinant surface display protein which is capable of tethering an electrocatalyst molecule, such as a cobalt(II) complex supported by tetradentate polypyridyl ligand 2-bis (2-pyridyl)(methoxy)methyl-6-pyridylpyridine (PY4), and enzymes for synthesizing a biologically derived compound, such as an alkane, alcohol, fatty acid, ester, or isoprenoid.

15 Claims, 13 Drawing Sheets

(56) References Cited

OTHER PUBLICATIONS

Schirmer, A., Rude, M.A., Li, X., Popova, E., Del Cardyre, S.B.: Microbial Biosynthesis of Alkanes. Science 2010, 329:559-562.

Steen, E.J., Kang. Y.S., Bokingsky, G. Hu, Z.H., Schirmer, A., McClure, A. Del Cardayre, S.B., Keasling, J.D.: Microbial production of fatty-acid-derived fuels and chemicals from plant biomass. Nature 2010, 463:559-U182.

Veiga, E., Sugawara, E., Nikaido, H., De Lorenzo, V., Fernandez, L.A.: Export of autotransported proteins proceeds through an oligomeric ring shaped by Cterminal domains. EMBO J 2002, 21:2122-2131.

IB-3131PCT, International Preliminary Report on Patentability, Appl. PCT/US2012/064216 dated May 5, 2015 (with Written Opinion of the International Searching Authority mailed May 22, 2013).

| Reductase / decarbonylase? | | 'tesA? | | Host |
|---|---|---|---|---|
| Promoter | Vector | Promoter | Vector | |
| $P_{ac}$ | pBBR1 | | | WT |
| | RFP | | | WT |
| $P_{ac}$ | pBBR1 | | | ΔphaCAB |
| | RFP | | | ΔphaCAB |
| $P_{ac}$ | pBBR1 | | | ΔphaC |
| | RFP | | | ΔphaC |
| $P_{BAD}$ | pBBR1 | | | WT |
| | GFP | | | WT |
| $P_{ac}$ | pKT230 | $P_{BAD}$ | pBBR1 | WT |
| | RFP | | GFP | WT |
| | | $P_{BAD}$ | pBBR1 | WT |
| | | | GFP | WT |
| | | | | ΔfadE (460, 1530) |
| $P_{ac}$ | pBBR1 | $P_{BAD}$ | pCM62 | ΔfadE (460, 1530) |
| | RFP | | RFP | ΔfadE (460, 1530) |
| $P_{ac}$ | pKT230 | $P_{BAD}$ | pBBR1 | ΔfadE (460, 1530) |
| | RFP | | GFP | ΔfadE (460, 1530) |

Figure 3

HYBRID ORGANIC-INORGANIC SYSTEM FOR PRODUCING BIOFUELS

RELATED PATENT APPLICATIONS

The application claims priority as a continuation application to PCT International Patent Application No. PCT/US2012/64216, filed Nov. 8, 2012, which claims priority to U.S. Provisional Patent Application Ser. No. 61/557,357, filed Nov. 8, 2011, both of which are hereby incorporated by reference in their entireties.

STATEMENT OF GOVERNMENTAL SUPPORT

The invention described and claimed herein was made utilizing funds supplied by the U.S. Department of Energy under Contract Nos. DE-AC02-05CH11231 and DE-0000206-1577 (Advanced Research Projects Agency-Energy Electrofuels Program). The government has certain rights in this invention.

FIELD OF THE INVENTION

The present invention is in the field of synthetic biology.

BACKGROUND OF THE INVENTION

Current efforts to produce biofuels using synthetic biology have focused on using model organisms (*E. coli* and *S. cerevisiae*) as chassis of metabolic engineering [1, 2]. These efforts have concentrated on using biomass-derived carbohydrates as the sources for renewable sources biofuel generation [3]. These strategies require redirection of central metabolic pathways by introduction of new pathways that redirect metabolic flux to a desired end-product. This approach has been used to produce alcohols, alkenes and isoprenoids that may be used as liquid fuel substitutes for petroleum [4]. Rewiring the metabolism of these model organisms so they can utilize $CO_2$ as the carbon input for biofuel production would have substantial benefits in broadening the substrate scope for metabolic engineering and reducing $CO_2$ emissions. However, transforming model organisms such as *E. coli* into an autotroph remains a daunting task that has not been accomplished.

One class of chemoautotrophic bacteria, "Knallgas" bacteria that grow with $H_2/CO_2$ under aerobic conditions, does not have these limitations. The model strain of this class, *Ralstonia eutropha*, can grow to very high cell densities (>200 g/L) and has been extensively manipulated genetically [5]. Under nutrient limitation, *R. eutropha* directs most of the reduced carbon flux generated by the Calvin cycle to synthesis of polyhydroxybutyrate (PHB), a biopolymeric compound stored in granules. Under growth with $H_2/CO_2$, 61 g/L of PHB was formed in 40 h, which represents ~70% of total cell weight (FIG. 1)[6]. PHB and related polyhydroxyalkonate polymers have been produced on industrial scale and marketed as Biopol™ (Monsanto; St. Louis, Mo.) and Mircel™ (Metabolix; Cambridge, Mass.) [5]. Therefore, *R. eutropha* is an attractive alternative for biofuel production from $CO_2$ as it already has the capability for autotrophic growth, is amenable to metabolic engineering and expresses a metabolic pathway that supports significant carbon flux.

An inexpensive source of $H_2$ will be essential for the effective development of *R. eutropha* as a biofuel-producing platform. Known small-molecule metal catalysts generally require organic acids, additives, and/or solvents that are also incompatible for use with living organisms [7]. Traditional catalysts in this area rely on sensitive thiol or phosphine donors, a key advance in this strategy is the choice of pyridine donors as a building block for ligand design, as they support water-stable and water-soluble complexes with reasonable reduction potentials based on strong s-donor/mild p-acceptor properties [8]. By using these rugged donor groups, inexpensive catalysts containing earth-abundant metal centers are accessible that are soluble and stable in microbial growth media. *R. eutropha* is an ideal microbe to couple with electrocatalysis, as growth with $H_2$ generated in situ by an electrode has already been demonstrated [9].

SUMMARY OF THE INVENTION

The present invention provides for a system for converting $CO_2$ and $H_2$ to one or more biologically derived compounds. In some embodiments, the system is an integrated microbial-electrocatalytic system for efficient conversion of $CO_2$ and $H_2$ to one or more biologically derived compounds. A unique aspect of this invention lies in the application of synthetic biology to integrate biological components and chemical components in a single chassis.

This invention is on the development of hybrid organic and in-organic components to enable improved biological systems. A unique aspect of this invention lies in the application of synthetic biology to integrate biological components (such as the host cell *Ralstonia eutropha* engineered to produce biofuels) and chemical components (such as polypyridine-ligands programmed to provide the source $H_2$) components in a single chassis which we term the Microbial-ElectroCatalytic (MEC) system. Whole cell biocatalytic systems have been developed previously for applications related to environmental remediation and biofuels production. Most of these applications however have primarily focused on the use of simple biologically derived catalysts such as phytochelatins, or proteins such as organophosphate hydrolase, cellulase and metallothionein to name a few. The area of blending organic and inorganic systems has the potential to address the limitations of enzyme-based catalysis through the use of robust, programmable inorganic alternatives while simultaneously maintaining the benefits of microbial processes such as low environmental impact and scalability.

The system comprises a source of molecular hydrogen and a host cell, such as a bacterium, capable of producing one or more biologically derived compounds. In some embodiments, the source of molecular hydrogen is one or more water-stable and water-soluble electrocatalyst molecules, such as a metal catalyst supported by a plurality of pyridine donors, such as a cobalt(II) complex supported by tetradentate polypyridyl ligand 2-bis(2-pyridyl)(methoxy)methyl-6-pyridylpyridine (PY4), which is an electrocatalyst for the reduction of protons to hydrogen and can operate in 50% aqueous media (its synthesis is described in Bigi et al., *Chemical Communications* 2010, 46:958-960, which is incorporated by reference). In some embodiments, the host cell is capable of expressing a recombinant surface display protein which is capable of tethering the electrocatalyst molecule (see FIG. 7 and Example 3).

The present invention can be applied various settings, such as in basic and applied research applications to understand how inorganic catalysts may be used to improve biological systems, in industry for manufacture of biologically derived compounds, and in medical applications where engineered bacteria may be used to perform specific reactions.

BRIEF DESCRIPTION OF THE DRAWINGS

The foregoing aspects and others will be readily appreciated by the skilled artisan from the following description of illustrative embodiments when read in conjunction with the accompanying drawings.

FIG. 3 shows the R. eutropha H16 strains tested for fatty acid production and alkane production. GFP and RFP-containing vectors served as controls. Strains are number 1-17. The variables are: genes (acyl-ACP reductase/decarbonylase, 'tesA), promoters ($P_{trc}$, $P_{BAD}$), vectors (pBBR1, pKT230, pCM62), and host genotype (wild-type, ΔphaCAB, ΔphaC, ΔfadE, (H16_A460, H16_A1530)).

DETAILED DESCRIPTION OF THE INVENTION

Figure 1:
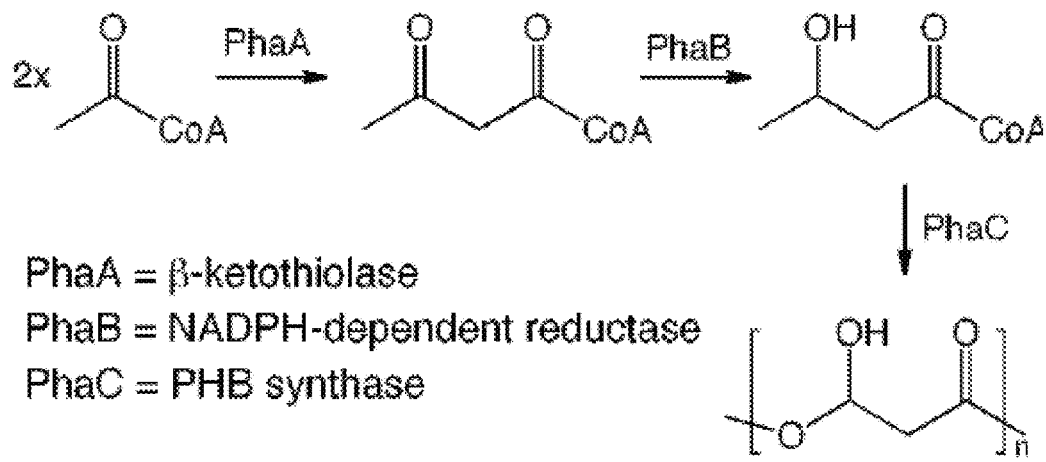
FIG. 1 shows the PHB synthesis pathway in R. eutropha.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The term "heterologous" as used herein refers to two compositions or material that are not found together in nature or not found as parts of a single species or individual organism in nature.

The present invention provides for a host cell comprising: (a) a first membrane-bound protein or peptide capable bound directly or indirectly to an electrocatalyst molecule, and (b) enzymes capable of synthesizing a biologically derived compound. In some embodiments, the host cell further comprises a second protein or peptide bound to the electrocatalyst molecule, wherein the first protein or peptide is bound to the second protein or peptide.

The present invention provides for a host cell comprising one or more nucleic acids encoding genes for a recombinant surface display protein or membrane-bound protein which is capable of tethering an electrocatalyst molecule and enzymes for synthesizing a biologically derived compound.

In some embodiments, the first and/or second protein or peptide is translocated to or outside of the outer membrane of the host cell upon expression within the host cell. In some embodiments, the membrane-bound protein or peptide is a transmembrane protein, such as *E. coli* FhuA. In some embodiments, the first and/or second protein or peptide can be a protein found in nature, or a functional variant thereof. In some embodiments, the membrane-bound protein or peptide comprises a transmembrane peptide and a membrane surface display peptide. In some embodiments, the transmembrane peptide and the membrane surface display peptide are heterologous to each other. In some embodiments, the first and/or second protein or peptide, or a part thereof, is heterologous to the host cell.

In some embodiments, the biologically derived compound is an alkane, alcohol, fatty acid, ester, or isoprenoid. In some embodiments, the electrocatalyst molecule is bound by a covalent bond to the first or second protein or peptide. In some embodiments, the electrocatalyst molecule is a cobalt (II) complex supported by tetradentate polypyridyl ligand 2-bis(2-pyridyl)(methoxy)methyl-6-pyridylpyridine (PY4). In some embodiments, the electrocatalyst molecule is a CdSe/ZnS nanoparticle, such as a nanocrystal as Qdot® nanocrystal (Life Technologies Corps., Cardsbad, Calif.).

In some embodiments, the host cell is a chemoautotroph capable of growth with $H_2/CO_2$ under aerobic conditions, such as a host cell of the genus *Ralstonia*. In some embodiments, the host cell is capable of using $CO_2$ as a carbon source. In some embodiments, the host cell is capable of growing to a high cell density, that is, equal to or more than 200 g/L. In some embodiments, the host cell can be artificially manipulated genetically. In some embodiments, the biologically derived compound is an organic compound such as an alkane, alcohol, fatty acid, ester, and/or isoprenoid. In some embodiments, the biologically derived compound can be used as a liquid fuel substitute for petroleum. Depending on the biologically derived compound synthesized by the system, the host cell is capable of expressing the necessary corresponding enzymes for synthesizing the biologically derived compound. In some embodiments, the host cell expresses the enzymes necessary for synthesizing biologically derived compound using $CO_2$ as a carbon source.

In some embodiments, the chemoautotroph is a lithoautotroph, such as a *Ralstonia* species. In some embodiments, the host cell is a *Ralstonia* species, such as *R. basilensis*, *R. campinensis*, *R. eutropha*, *R. gilardii*, *R. insidiosa*, *R. mannitolilytica*, *R. metallidurans*, *R. paucula*, *R. pickettii*, *R. respiraculi*, *R. solanacearum*, *R. syzygii*, or *R. taiwanensis*. In some embodiments, the host cell is *R. eutropha* H16.

In some embodiments, the host cell comprises one or more nucleic acid encoding the recombinant surface display protein and/or enzymes for synthesizing the biologically derived compound. In some embodiments, genes encoding the recombinant surface display protein and the enzymes for synthesizing the biologically derived compound are located on one or more nucleic acids. In some embodiments, the nucleic acids are capable of stable residence within the host cell. In some embodiments, the nucleic acids are vectors or expression vectors. In some embodiments, the nucleic acids are stably integrated in the bacterial chromosome. In some embodiments, the genes are recombinant and introduced into the host cell. In some embodiments, one or more genes for synthesizing the biologically derived compound are native to the host cell.

A unique aspect of this invention lies in the application of synthetic biology to integrate the aforementioned biological components (such as *R. eutropha* engineered to produce biofuels) and chemical components (such as polypyridine-ligands programmed to provide the source $H_2$) components in a single chassis—the Microbial-ElectroCatalytic (MEC) system. Whole cell biocatalytic systems have been developed previously for applications related to environmental remediation and biofuels production [10, 11]. Most of these applications however have primarily focused on the use of simple biologically derived catalysts such as phytochelatins [12], or proteins such as organophosphate hydrolase [13], cellulase [14] and metallothionein [15] to name a few. The area of blending organic and inorganic systems, while relatively a new one [16, 17], has the potential to address the limitations of enzyme-based catalysis through the use of robust, programmable inorganic alternatives while simultaneously maintaining the benefits of microbial processes such as low environmental impact and scalability.

In some embodiments, the system comprises a host cell comprising one or more nucleic acids encoding genes for a recombinant surface display protein which is capable of tethering the electrocatalyst molecule and enzymes for synthesizing the biologically derived compound.

The integrated MEC (Microbial-ElectroCatalytic) system, the combination of a novel catalytic system to generate $H_2$ directly from water coupled to a chemolithoautotroph, *R. eutropha*, that is metabolically engineered to produce high titers of biofuels from $H_2$ and $CO_2$, will be a transformative technology that will provide a new source of renewable liquid transportation fuels that extends beyond biomass-derived substrates. This system will provide a template for the eventual introduction of water-splitting catalysts that will generate $H_2$ and $O_2$ with light in the presence of biofuel-producing microorganisms.

Production of Hydrocarbons by *Ralstonia eutropha* Through Fatty Acid Metabolism Using a synthetic biology approach, *R. eutropha* H16 is engineered to produce fatty acid-derived hydrocarbon biofuels.

*R. eutropha* H16 has been engineered for production of alkanes through the acyl-ACP reductase/aldehyde decarbonylase pathway from *S. elongates* [18]. Expression of the acyl-ACP reductase/aldehyde decarbonylase pathway in *R. eutropha* H16 produced pentadecane at ~30 µg/L by formal decarboxylation of palmitic acid. Secondly, the oleABCD pathway has been constructed in *R. eutropha* H16 which is tested for alkene production [19].

Figure 2:
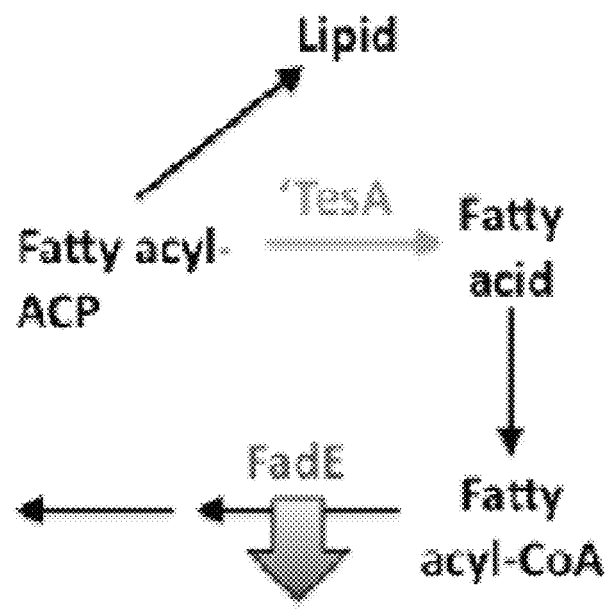
FIG. 2 shows the proposed strategy to overproduce fatty acids in R. eutropha H16.

To increase the titer of hydrocarbon production in *R. eutropha* H16, overproduction of fatty acids is accomplished through insertion of a thioesterase (*E. coli* 'tesA) into *R. eutropha* H16 which has previously been shown to deregulate fatty acid biosynthesis and increase fatty acid production in *E. coli* [20]. The strategy also involves in-frame deletions of two homologs of fadE (A0460 and A1530) in *R. eutropha* H16, which catalyzes the β-oxidation of fatty acyl-CoA (FIG. 2).

Figure 4:
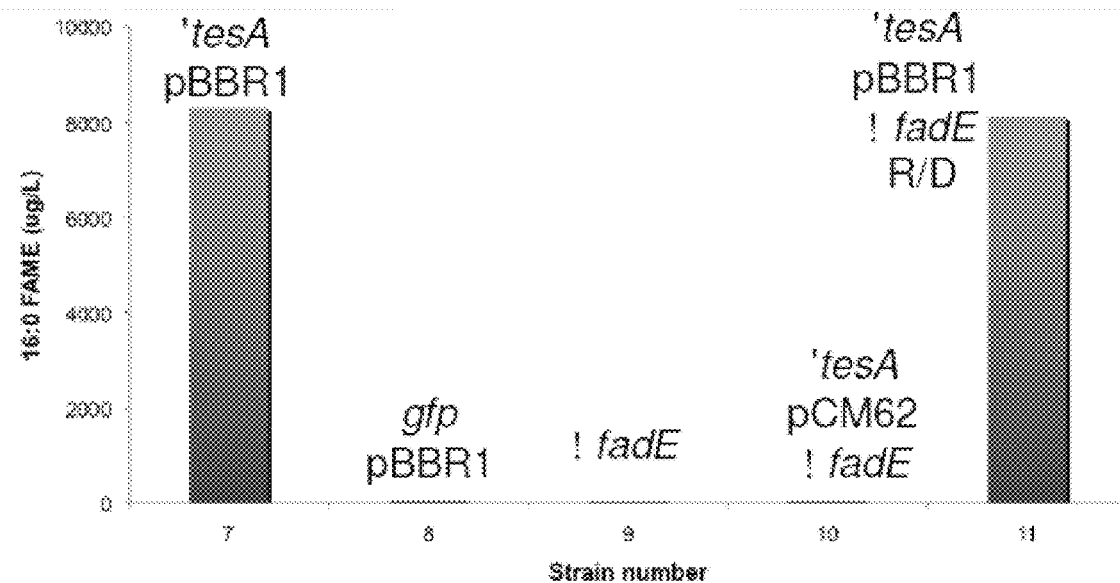
FIG. 4 shows fatty acid over-production in strains of R. eutropha.
Figure 5:
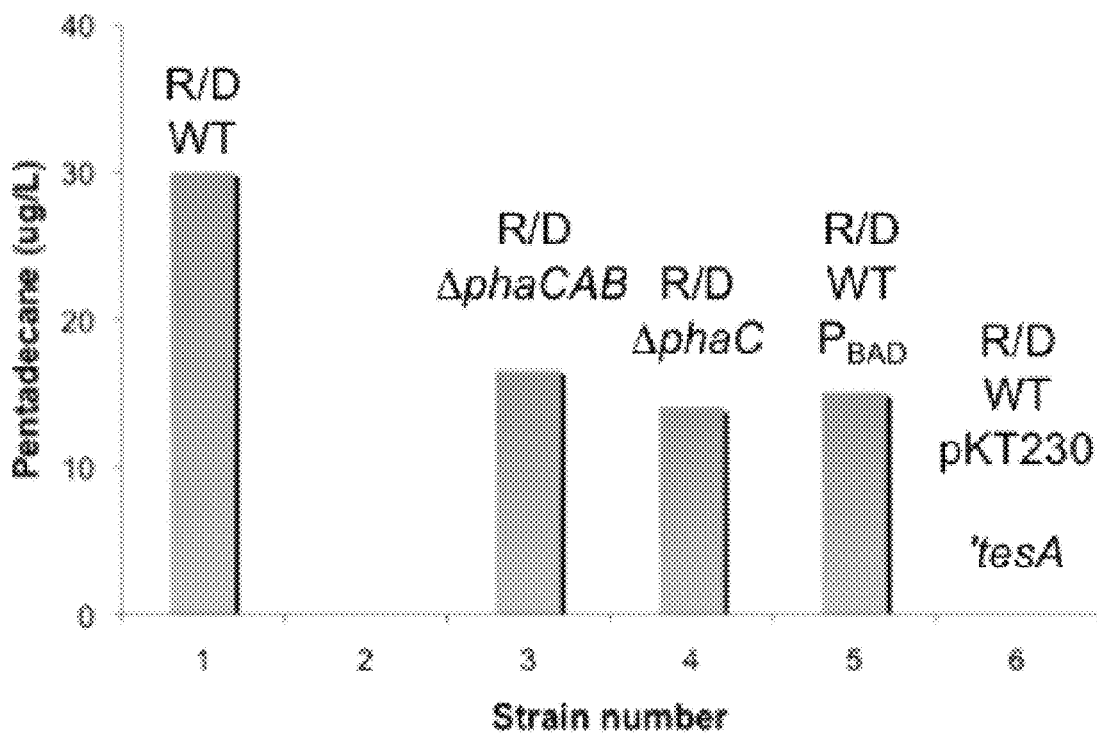
FIG. 5 shows alkane production in R. eutropha strains.

To test fatty acid overproduction and its relationship with alkane production, strains of *R. eutropha* described in FIG. 3 is constructed and cultured in LB to determine initial levels of fatty acids and alkanes. Introduction of 'tesA into an *R. eutropha* wild-type background generates a strain that produces >150× palmitic acid (16:0) compared to wild-type (FIG. 4). Unexpectedly, in frame deletion of two fadE homologs do not increase fatty acid levels in the strain that expresses 'tesA. Introduction of 'tesA on plasmid vector pCM62, which has a lower copy number compared to pBBR1, generates a strain that does not overproduce fatty acids relative to wild type. Additionally, constructs with acyl-ACP reductase and aldehyde decarbonylase in *R. eutropha* ΔphaCAB and ΔphaC strains produce half the amount of alkane compared to the wild-type background (FIG. 5). Co-expressing 'tesA and the alkane production genes result in almost no production of alkane. The fatty acid and hydrocarbon production can be tested under both heterotrophic and autotrophic conditions in minimal media in wild-type and PHB⁻ mutants. In these cultures in minimal media, the production is tested under conditions that promote PHB biosynthesis and expect to divert the substantial carbon flux through this pathway towards biofuels when growing *R. eutropha* H16 under these conditions.

Production of Hydrocarbons from *Ralstonia eutropha* by Isoprenoid Metabolism

The isoprenoid pathway represents an important source of advanced biofuel precursors such as farnesene. Chemical hydrogenation of farnesene produces farnesane, which can serve as a fungible fuel. All terpenoids originate from the same universal precursors [isopentenyl pyrophosphate (IPP) and its isomer dimethylallyl pyrophosphate (DMAPP)] that are generated through two known biosynthetic pathways—the mevalonate-dependent (MEV) isoprenoid pathway mostly found in eukaryotes and the deoxyxylulose 5-phosphate (DXP) pathway found in most prokaryotes. The *R. eutropha* genome encodes the DXP pathway, which generates the precursor molecules IPP and DMAPP demonstrated to be essential in prokaryotes for the prenylation of tRNAs and the synthesis of farnesyl pyrophosphate (FPP), which is used for quinone and cell wall biosynthesis [21]. While farnesene may be produced in *R. eutropha* through the manipulation of its native DXP pathway, the tight regulation of essential metabolites produced through this route may pose a significant challenge in achieving reasonable titers. In one embodiment, for the production of isoprenoid-based fuel molecules by *R. eutropha*, the pathway incorporates the MEV pathway.

Figure 6:
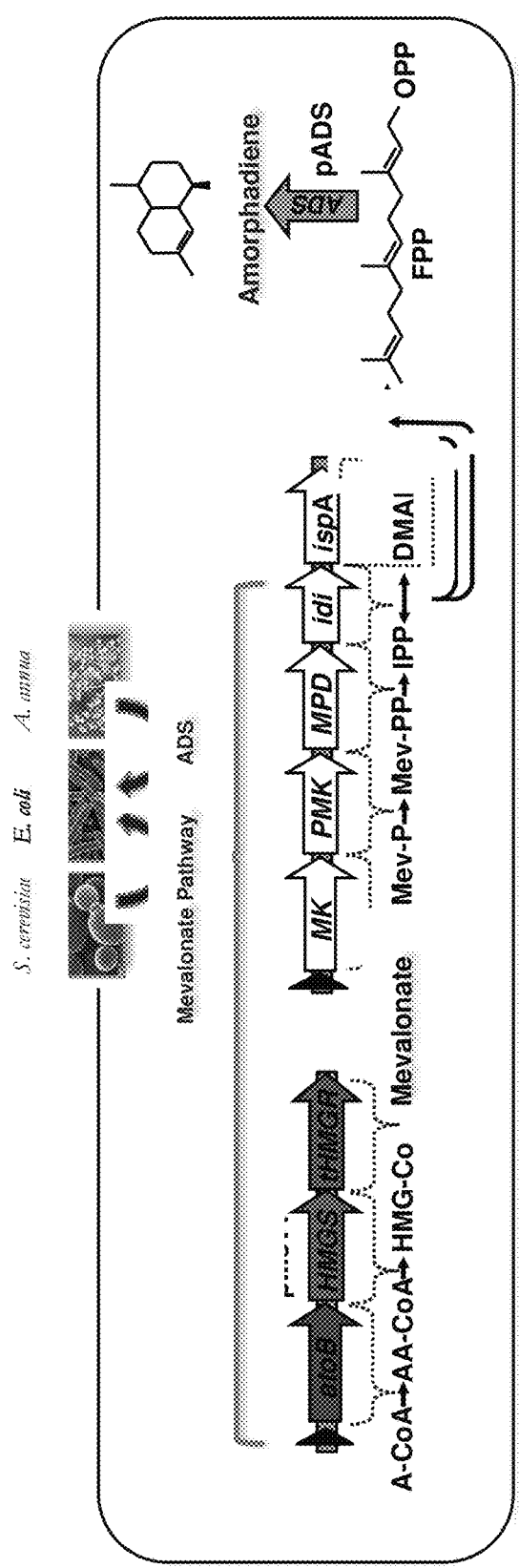
FIG. 6 shows the mevalonate pathway for production of isoprenoids in Ralstonia eutropha.

The genes originating from distinct prokaryotic and eukaryotic sources is synthesized to enable production of α-farnesene in the in *R. eutropha* base chassis (FIG. 6). All heterologous genes are chemically synthesized to match the native codon usage of *R. eutropha*. The MEV pathway genes is synthesized using sequence information from the genome of *Borrelia burgdorferi* [22]. This spirochaete carries a dedicated isoprenoid biogenesis operon that encodes all five enzymes of the aforementioned pathway leading from acetoacetyl-CoA to IPP. These include 3-hydroxy-3-methylglutaryl-CoA synthase (HMGS; BB0683), 3-hydroxy-3-methylglutaryl-CoA reductase (HMGR; BB0685), mevalonate kinase (MK; BB0688), phosphomevalonate kinase (PMK; BB0687) and mevalonate pyrophosphate decarboxylase (PMD; BB0686). This operon also encodes isopentenyl-diphosphate isomerase (BB0684) required for the isomerization of IPP to DMAPP. The *R. eutropha* genome encodes for IspA, which is required for the next step in the pathway, the synthesis of farnesyl pyrophosphate (FPP) from IPP and DMAPP. Finally conversion of FPP to α-farnesene is accomplished by synthetic α-farnesene synthase (FAS) from *Pyrus bretschneideri* which is also optimized for expression in *R. eutropha*. The aforementioned operon is assembled either in the form of multiple expression vectors or suicide constructs (for chromosomal integration) depending on observed stability of the former.

Along with the mevalonate pathway, codon-optimized genes from amophadiene synthase, farnesene synthase, bisabolene synthase and squalene synthase are chemically synthesized. Amorphadiene synthase (*Artemisia annua*) is on the pBBr1 vector under the control of the pBAD promoter. Under growth in LB, this construct produces 2 mg/L of amorphadiene in a dodecane overlay.

The electrocatalyst molecules are tethered to the surface of *R. eutropha* through recombinant surface display proteins. To enable site specific labeling, these proteins is engineered to code for an 'aldehyde' tag (A-tag) with the following consensus sequence: Leu-Cys-Thr-Pro-Ser-Arg (SEQ ID NO:1). This 6-amino acid tag was recently demonstrated to serve as an efficient chemical handle for labeling applications [23]. This technique relies on selective post-translational modification of the Cys residue from this tag to an aldehyde by a formylglycine generating enzyme (FGE). The aldehyde group is derivatized on surface display proteins, with an appropriately synthesized aminooxy-containing hydrogen catalyst. The synthetic flexibility of this platform will allow for optimization of conjugation affinities and surface-attached catalyst performance.

Figure 7:
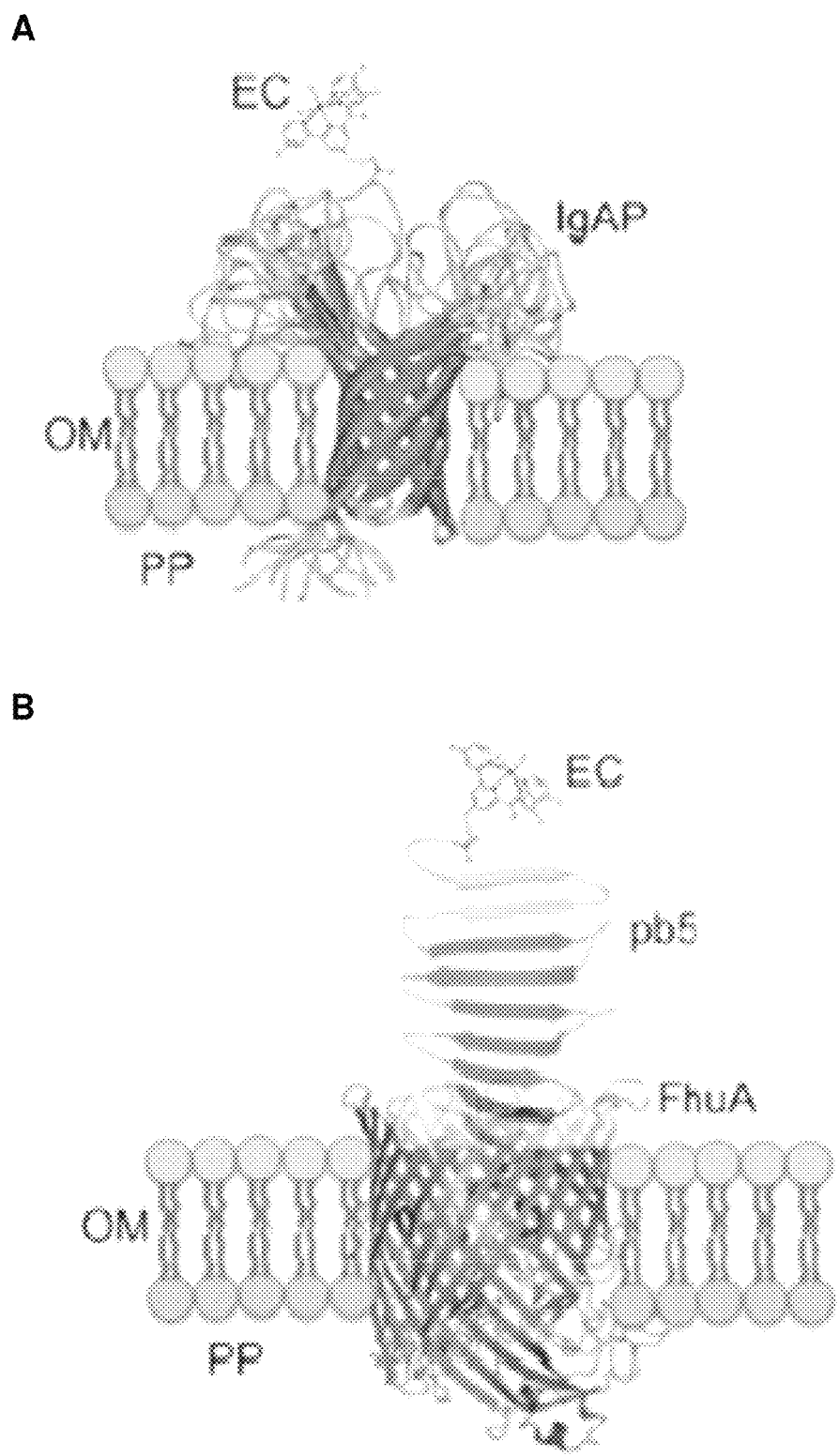
FIG. 7 shows two strategies (A and B) for binding of electrocatalysts to the surface of R. eutropha. OM is "outer membrane", PP is "periplasm", EC is "electrocatalyst", IgAP is "IgA protease" (N. gonorrhoeae), Pb5 is "receptor binding protein" (bacteriophage T5), FhuA is outer membrane iron-transporter (E. coli).

There are two different approaches for A-tag based surface tethering of the catalyst (FIG. 7). In the first approach the A-tag is directly present on a recombinant protein expressed on the cell surface, whereas in the second approach the A-tag is present on an exogenous protein that tightly interacts with another recombinant cell surface protein. *R. eutropha* has been previously engineered to express an autotransporter protein secretion system to anchor functional mouse metallothionein molecules onto its cell surface, to enable sequestration of heavy metals from toxic environments [15].

Autotransporters are a widespread family of secreted proteins found in Gram-negative bacteria that are able to independently translocate through the outer membrane and have been successfully used to display a variety of proteins on bacterial cell surfaces [24]. A slight variant of the aforementioned autotransporter protein secretion scheme is engineered; the system anchors a hybrid protein engineered to contain an N-terminal signal peptide followed by A-tag fused to the C-terminal domain of the IgA protease (C-IgAP) from *Neisseria gonorrhoeae* for cell surface display in *R. eutropha*. From similar work in *E. coli* [25], this system should result in fully exposed A-tag residues, being involved in the conjugation reaction with the electrocatalyst.

In the second approach, the native ability of two cell surface proteins to molecularly interact with each other is exploited—the bacteriophage T5 receptor-binding protein, pb5, and the outer membrane iron-transporter, FhuA, of *E. coli*. This approach enables decoupling the conjugation reaction and cell surface protein expression steps and allows tighter control in generation of the MEC system. The molar stoichiometric ratio of pb5 and FhuA in the complex formed by these proteins is one as demonstrated by in-vitro and in-vivo studies [26]. Amino acid residues necessary for molecular interaction between pb5 and FhuA have also been deciphered [27]. Separately, using *E. coli* as the host, a $His_6$- and A-tagged form of pb5 is overexpressed and purified. Purified pb5 is conjugated to the electrocatalyst through the A-tag and subsequently added to a growing pool of engineered *R. eutropha* expressing FhuA on its cell surface. The molecular interaction between pb5 and FhuA should localize the electrocatalyst on the microbial cell surface.

References cited in the present specification (except Example 4):

1. Dellomonaco C, Fava F, Gonzalez R: The path to next generation biofuels: successes and challenges in the era of synthetic biology. *Microbial Cell Factories* 2010, 9.
2. Clomburg J M, Gonzalez R: Biofuel production in *Escherichia coli*: the role of metabolic engineering and synthetic biology. *Applied Microbiology and Biotechnology* 2010, 86:419-434.
3. Keasling J D, Chou H: Metabolic engineering delivers next-generation biofuels. *Nature Biotechnology* 2008, 26:298-299.
4. Fortman J L, Chhabra S, Mukhopadhyay A, Chou H, Lee T S, Steen E, Keasling J D: Biofuel alternatives to ethanol: pumping the microbial well. *Trends in Biotechnology* 2008, 26:375-381.
5. Reinecke F, Steinbuchel A: *Ralstonia eutropha* Strain H16 as Model Organism for PHA Metabolism and for Biotechnological Production of Technically Interesting Biopolymers. *Journal of Molecular Microbiology and Biotechnology* 2009, 16:91-108.
6. Ishizaki A, Tanaka K, Taga N: Microbial production of poly-D-3-hydroxybutyrate from $CO_2$. *Applied Microbiology and Biotechnology* 2001, 57:6-12.
7. Gloaguen F, Rauchfuss T B: Small molecule mimics of hydrogenases: hydrides and redox. *Chemical Society Reviews* 2009, 38:100-108.
8. Bigi J P, Hanna T E, Harman W H, Chang A, Chang C J: Electrocatalytic reduction of protons to hydrogen by a water-compatible cobalt polypyridyl platform. *Chemical Communications* 2010, 46:958-960.
9. Schlegel H G, Lafferty R: Growth of Knallgas bacteria (Hydrogenomonas) using direct electrolysis of culture medium. *Nature* 1965, 205:308-&.
10. Lee S Y, Choi J H, Xu Z: Microbial cell-surface display. *Trends Biotechnol* 2003, 21:45-52.
11. Wu C H, Mulchandani A, Chen W: Versatile microbial surface-display for environmental remediation and biofuels production. *Trends Microbiol* 2008, 16:181-188.
12. Bae W, Chen W, Mulchandani A, Mehra R K: Enhanced bioaccumulation of heavy metals by bacterial cells displaying synthetic phytochelatins. *Biotechnol Bioeng* 2000, 70:518-524.
13. Richins R D, Kaneva I, Mulchandani A, Chen W: Biodegradation of organophosphorus pesticides by surface-expressed organophosphorus hydrolase. *Nat Biotechnol* 1997, 15:984-987.
14. Fujita Y, Takahashi S, Ueda M, Tanaka A, Okada H, Morikawa Y, Kawaguchi T, Arai M, Fukuda H, Kondo A: Direct and efficient production of ethanol from cellulosic material with a yeast strain displaying cellulolytic enzymes. *Appl Environ Microbiol* 2002, 68:5136-5141.
15. Valls M, Atrian S, de Lorenzo V, Fernandez L A: Engineering a mouse metallothionein on the cell surface of *Ralstonia eutropha* CH34 for immobilization of heavy metals in soil. *Nature Biotechnology* 2000, 18:661-665.
16. Jose J, Bernhardt R, Hannemann F: Functional display of active bovine adrenodoxin on the surface of *E. coli* by chemical incorporation of the [2Fe-2S] cluster. *Chembiochem* 2001, 2:695-701.
17. Baxter-Plant V S, Mikheenko I P, Robson M, Harrad S J, Macaskie L E: Dehalogenation of chlorinated aromatic compounds using a hybrid bioinorganic catalyst on cells of *Desulfovibrio desulfuricans*. *Biotechnol Lett* 2004, 26:1885-1890.
18. Schirmer A, Rude M A, Li X, Popova E, del Cardayre S B: Microbial Biosynthesis of Alkanes. *Science* 2010, 329:559-562.
19. Beller H R, Goh E B, Keasling J D: Genes Involved in Long-Chain Alkene Biosynthesis in *Micrococcus luteus*. *Applied and Environmental Microbiology* 2010, 76:1212-1223.
20. Steen E J, Kang Y S, Bokinsky G, Hu Z H, Schirmer A, McClure A, del Cardayre S B, Keasling J D: Microbial production of fatty-acid-derived fuels and chemicals from plant biomass. *Nature* 2010, 463:559-U182.
21. Pohlmann A, Fricke W F, Reinecke F, Kusian B, Liesegang H, Cramm R, Eitinger T, Ewering C, Potter M, Schwartz E, et al: Genome sequence of the bioplastic-producing "Knallgas" host cell *Ralstonia eutropha* H16. *Nat Biotechnol* 2006, 24:1257-1262.
22. Fraser C M, Casjens S, Huang W M, Sutton G G, Clayton R, Lathigra R, White O, Ketchum K A, Dodson R, Hickey E K, et al: Genomic sequence of a Lyme disease spirochaete, *Borrelia burgdorferi*. *Nature* 1997, 390:580-586.
23. Carrico I S, Carlson B L, Bertozzi C R: Introducing genetically encoded aldehydes into proteins. *Nature chemical biology* 2007, 3:321-322.
24. Jose J, Meyer T F: The autodisplay story, from discovery to biotechnical and biomedical applications. *Microbiol Mol Biol Rev* 2007, 71:600-619.
25. Veiga E, Sugawara E, Nikaido H, de Lorenzo V, Fernandez L A: Export of autotransported proteins proceeds through an oligomeric ring shaped by C-terminal domains. *EMBO J* 2002, 21:2122-2131.
26. Plançon L, Janmot C, le Maire M, Desmadril M, Bonhivers M, Letellier L, Boulanger P: Characterization of a high-affinity complex between the bacterial outer membrane protein FhuA and the phage T5 protein pb5. *J Mol Biol* 2002, 318:557-569.
27. Mondigler M, Holz T, Heller K J: Identification of the receptor-binding regions of pb5 proteins of bacteriophages T5 and BF23. *Virology* 1996, 219:19-28.

The above references are incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Metabolic Engineering of *Ralstonia eutropha* for Biofuel Production

The following is a series of steps for genetic engineering *Ralstonia eutropha* to alter PHB and fatty acid production, construct plasmid vectors containing genes for biofuel production and transformation into *R. eutropha*, produce butanol and alkenes from $H_2/CO_2$ with metabolically engineered *R. eutropha*, and express cell surface proteins by *R. eutropha* for conjugation to electrocatalyst.

Construction of one plasmid vector with complete biofuel pathway for either butanol (three gene construct) or alkene (up to seven gene construct) production.

Demonstration of transformation efficiency for *R. eutropha* of >100 kanamycin-resistant colonies/μg DNA.

Generation of one defined mutant of *R. eutropha* with no detectable PHB under autotrophic growth conditions.

Generation of one defined mutant of *R. eutropha* with pyruvate excreted at >1 mM under autotrophic growth conditions.

Cell surface display of Green Fluorescent Protein (GFP) in *R. eutropha* with tunable expression (ranging from 5~50 outer membrane proteins/cell).

Generation of *R. eutropha* mutant with 3× increased production of fatty-acid compared to wild-type.

Construction of all essential plasmid vectors with complete pathways for butanol (three gene construct) and alkene (three and seven gene constructs) production.

Transformation of chromosomally engineered *R. eutropha* mutants with plasmids for butanol and alkene production at >100 kanamycin-resistant colonies/μg DNA.

Detection of expressed pathway proteins coded on plasmids using Multi-Reaction Monitoring method of targeted peptide mass spectrometry.

Attachment of electrocatalyst to engineered *Ralstonia* strains (ranging from 5~50 molecules/cell).

Production of butanol or alkene products at >10 mg/L from $H_2/CO_2$.

Production of butanol at >10 mg/L from $H_2/CO_2$.

Production of alkene at >100 mg/L from $H_2/CO_2$.

Production of butanol or alkene product from $H_2/CO_2$ in 1 L bioreactor at >10 mg/L.

EXAMPLE 2

Integration of Electrocatalytic $H_2$ Generation with Biofuel Production by Engineered *R. eutropha* Strains The following is a series of steps for autotrophic growth of *R. eutropha* in presence of soluble electrocatalyst, generation of biofuel products from engineered *R. eutropha* strains in the presence of electrocatalyst using electricity/$CO_2$, tethering of electrocatalyst to cell surface of *R. eutropha*, and conversion of electricity/$CO_2$ to biofuels using electrocatalyst/*R. eutropha* bioconjugates.

Production of $H_2$ in *R. eutropha* growth medium at >200 mol $H_2$/mol of catalyst/hr.

Heterotrophic growth of *R. eutropha* in the presence of >1 μm of electrocatalyst.

Synthesis of one derivative each of the PY5 ligand containing alkyne, thiol and halogen group.

Conjugation of MoPY5 complexes to electrode surfaces and production of >200 mol $H_2$/mol of catalyst/hr.

Optimization of electrocatalyst properties in *R. eutropha* growth medium (<200 mV overpotential, >1000 mol $H_2$/mol of catalyst/hr).

Demonstration production of PHB (>1 g/L) by WT *R. eutropha* with electricity/$CO_2$ in the presence of soluble electrocatalyst.

Demonstration of growth of production of pyruvate (>100 μM) by mutant *R. eutropha* strain with electricity/$CO_2$ in the presence of soluble electrocatalyst.

Demonstration of production of PHB (>500 mg/L) by *R. eutropha* strains with tethered electrocatalyst from electricity/$CO_2$.

Production of butanol from metabolically engineered strain tethered to electrocatalyst at >1 mg/L from electricity/$CO_2$.

EXAMPLE 3

As a first step to conjugating electrocatalysts to the surface of *R. eutropha*, the export of proteins with functional groups for conjugation to synthetic inorganic complexes is required. A dual strategy is conceived to conjugate these complexes to the outer membrane surface of *R. eutropha* (FIG. 7).

To establish that IgA and FhuA could be exported to the membrane, Red Fluorescent Protein (RFP) is engineered into constructs containing these proteins and expressed in *R. eutropha*. Control strains contain the gene for RFP on vectors lacking the FhuA and IgA genes.

Figure 8:
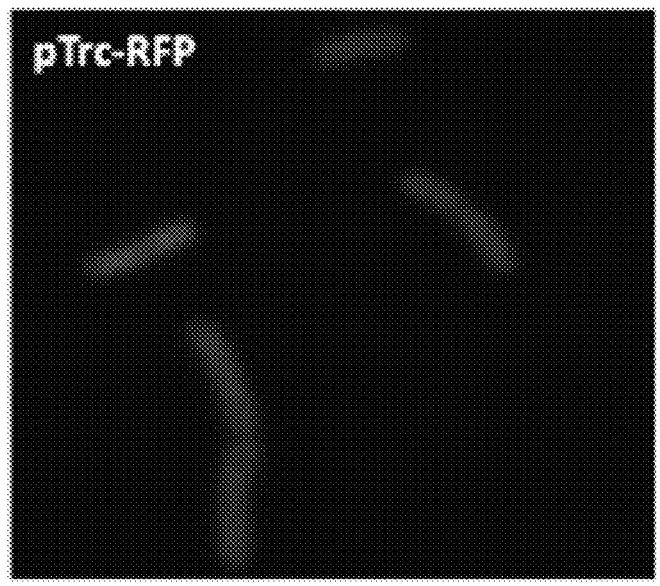
FIG. 8 shows the fluorescence microscopy of R. eutropha with RFP alone.
Figure 9:
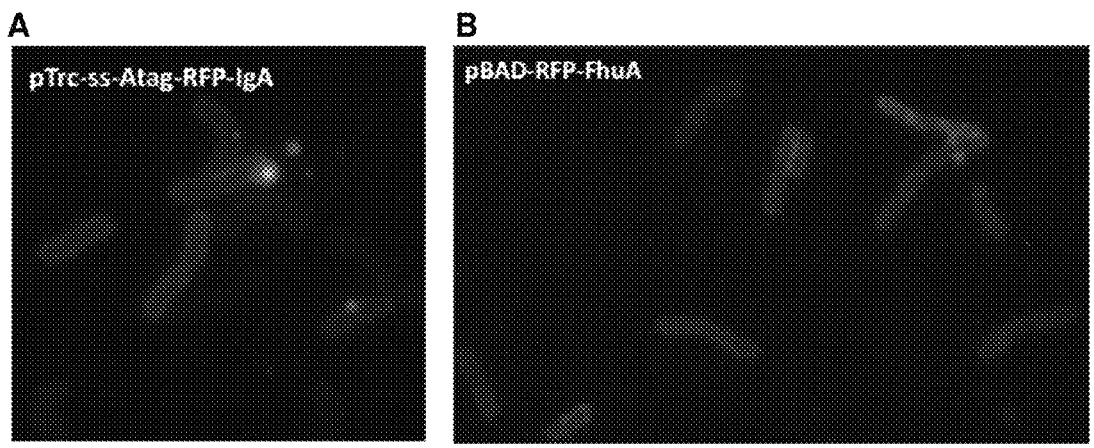
FIG. 9 shows the expression of IgA and FhuA with fused RFP on the outer membrane of R. eutropha: a) IgA; b) FhuA.

The pBBR1 vectors used for protein expression are controlled by $P_{trc}$ and $P_{BAD}$ promoters. Preliminary work with pBBR1-RFP driven by the $P_{trc}$ promoter demonstrates that this promoter is leaky and show no inducible activity with IPTG. In contrast, pBBR1-RFP driven by the $P_{BAD}$ shows almost no constitutive expression and is inducible with 0.2% arabinose. Epifluorescence microscopy performed on the constructs with only RFP demonstrated that the protein is broadly distributed in the cytoplasm of *R. eutropha* (FIG. 8). Fusing the RFP gene to genes coding for IgA and FhuA causes substantial changes in the observed expression pattern of RFP (FIG. 9*a-b*). Expression of these fused proteins is at the surface of *R. eutropha* cells, with no apparent expression in the interior of the cells. In addition, outer-membrane vesicles, often observed with gram-negative bacteria, contain substantial amounts of RFP. Based on the observation of unbroken fluorescence at the surface of the *R. eutropha*, we estimate that >1000 molecules of RFP-IgA are present on the surface of the cells. Also, we are able to tune the expression by using vectors containing pBAD.

Figure 10:
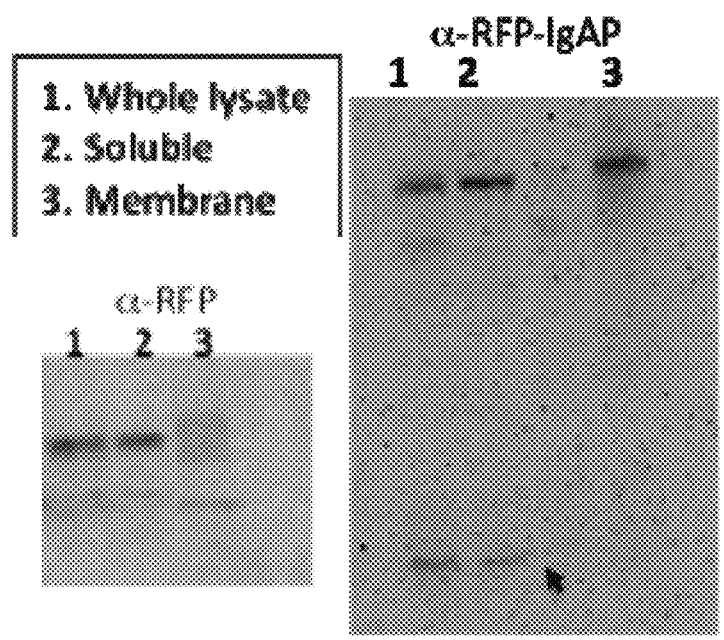
FIG. 10 shows the cross-reaction of RFP with anti-RFP antibody in R. eutropha constructs containing RFP (left panel) and RFP-IgA protein (right panel).

We have also demonstrated the localization of RFP to the outer membrane by fractionating *R. eutropha* cells into soluble and membrane fractions. In the control cultures with RFP only, the antibody detects almost no RFP in the membrane fraction; however, a substantial cross-reaction is observed for the membrane fraction of the RFP-IgA fusion (FIG. 10). We have constructed version of the IgA protein with the A-tag sequence, and co-expressed this construct in *R. eutropha* with a codon-optimized version of Mycohost cell tuberculosis FGE, and the effectiveness of A-tag binding to the surface of *R. eutropha* with fluorescently labeled small molecules and inorganic complexes is determine as described below.

Figure 11:
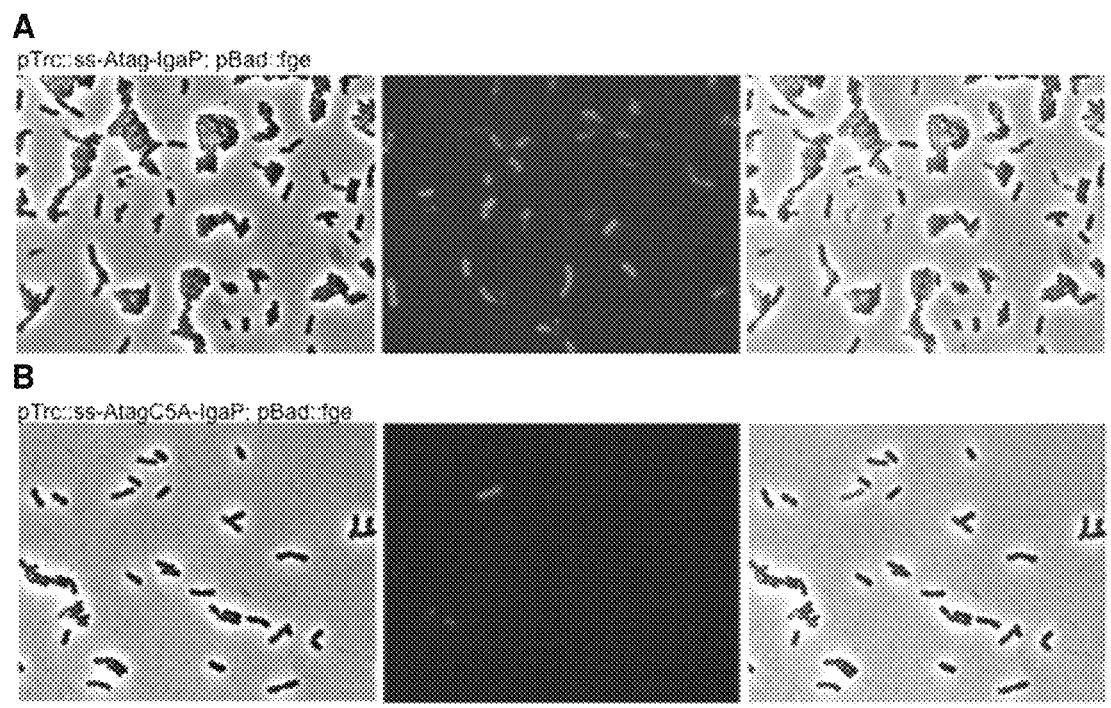
FIG. 11 shows the phase contrast and fluorescent microscopy showing the binding of flourophore to A-tag sequence expressed by R. eutropha (A) and control (B).

To develop conditions to bind the electrocatalysts to these cell surface proteins, a commercially available fluorescent compound (Alexa Fluor 647 C5-aminooxyacetamide) is used to test surface binding. This fluorophore containing compound is incubated with *R. eutropha* strains containing an A-tag linker bound to the IgA protease domain and compared to a control where the site of A-tag linkage (Cys residue) was varied to an Ala. FIG. 11 shows phase contrast and fluorescent microscopy of the A-tag version and the control. The fluorescent image depicts more labeling in the A-tag version compared to the control. However, subsequent experiments show that the extent of labeling varies. Experiments has shown that a $Ru(bipy)^{2+}$ derivative also binds to the A-tag.

It is also demonstrated that the pb5 protein, expressed in an *E. coli* background with an overexpressed FGE, contains an active A-tag. The pb5 protein is derivatized with a biotin hydrazide and the binding of biotin demonstrated by cross-reaction with an antibody that recognizes biotin.

EXAMPLE 4

Functionalizing Bacterial Cell Surfaces with a Phage Protein

Functionalization of bacterial cell surfaces has the potential to introduce new activities by chemical modification. Here we show that a bacteriophage-receptor complex can be used to functionalize the surface of two Gram-negative proteobacteria, *Escherichia coli* and *Ralstonia eutropha* with CdSe/ZnS nanoparticles. This work highlights the potential for using microbe-phage interactions to generate new functions in living cells.

Controlled functionalization of living cell surfaces alters cell biology and creates new biological activities[1, 2]. This strategy has been exploited in living mammalian cells using bio-orthogonal chemistry targeting specific functional groups on the cell surface.[3]

Functionalizing the cell surfaces of bacteria has the potential to introduce new activities by chemical modification.[4] However, relatively few general methods have been reported for the functionalization of bacterial cell surfaces and these techniques often utilize non-specific binding mechanisms for surface interactions.[5, 6] Exploiting highly specific interactions with the bacterial outer membrane will allow controlled functionalization of the cell surface. Bacteriophages recognize specific receptor proteins on the bacterial cell surface for protein-protein binding and injection of viral DNA.[7] Though these complexes have been studied extensively in vitro, the potential of these complexes as modules to functionalize living cells by in vivo expression has not been explored.

Figure 12:
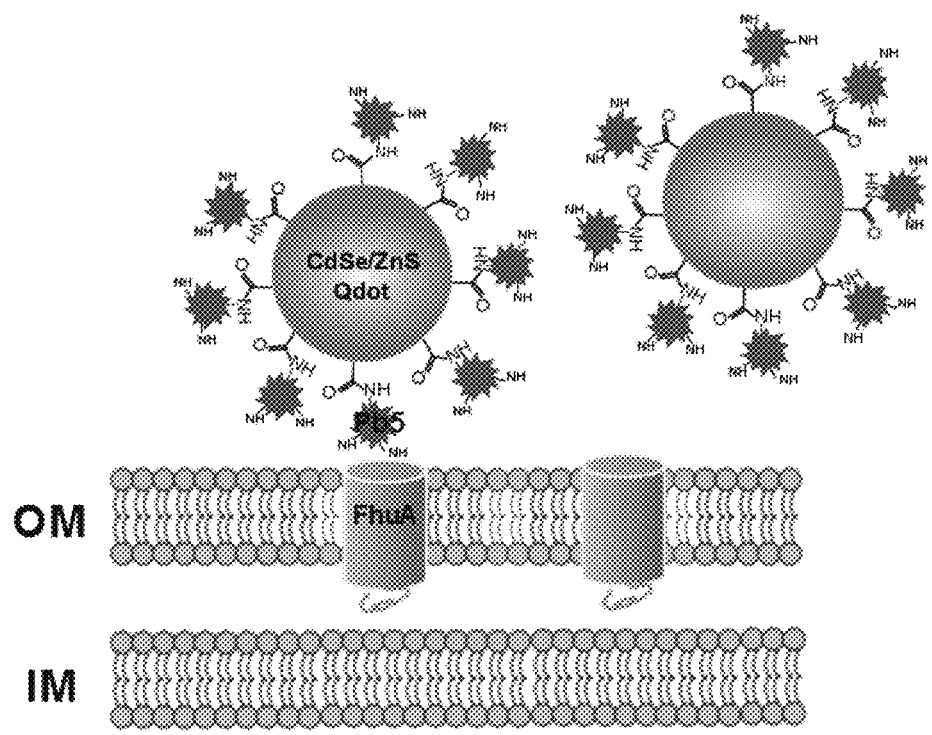
FIG. 12 shows a schematic illustration of FhuA-specific labeling using Qdot-pb5 conjugate. OM: outer membrane; IM: inner membrane.

The protein-protein complex formed between *E. coli* FhuA, an outer membrane iron transporter protein[8, 9] and pb5, a phage protein expressed by bacteriophage T5, was chosen for cell functionalization (FIG. 12) because the protein complex is stable and has been characterized by biophysical and biochemical techniques[7, 9, 10]. *E. coli* was chosen as the initial host to demonstrate the interaction in vivo because it is the native organism for the interaction and *R. eutropha* H16 was chosen because of its biotechnological potential in the production of biofuels and biochemicals from $CO_2$[11, 12].

Figure 16:
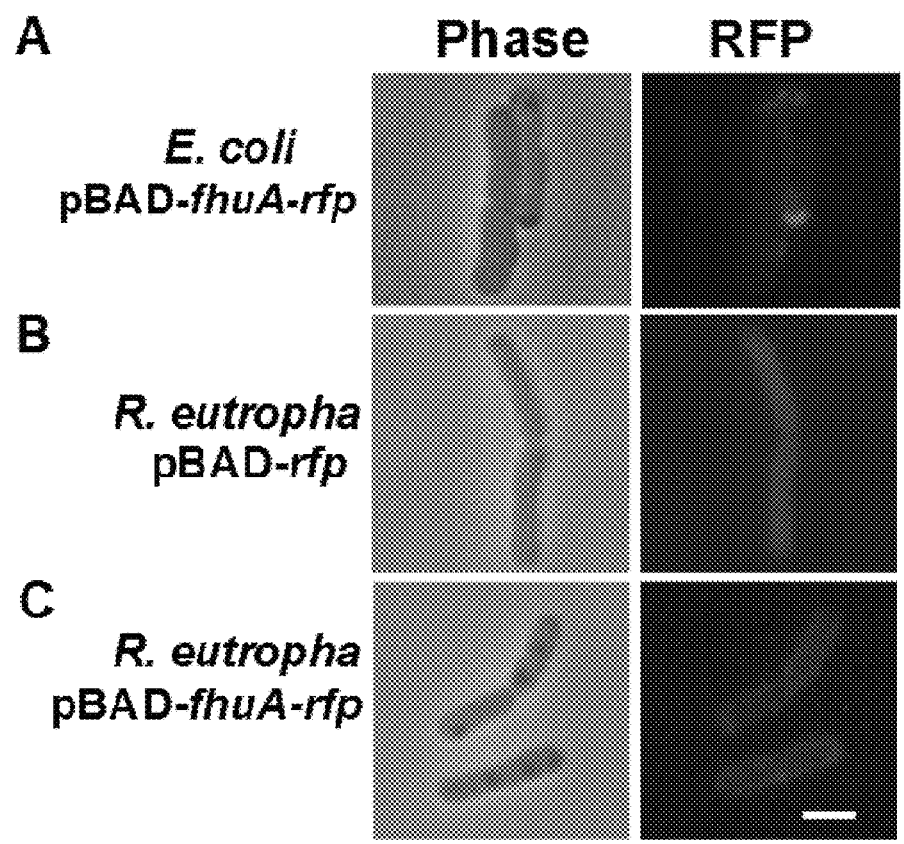
FIG. 16 shows fluorescence microscopy images of cell-selective imaging of (A) E. coli expression of FhuA-RFP (B) R. eutropha with RFP alone (C) R. eutropha expression of FhuA-RFP fusion. Scale bar: 1 µm.

FhuA was exported to the outer membrane under controlled conditions to demonstrate the in vivo interaction between FhuA and pb5. In *E. coli*, FhuA was overexpressed and its export to the outer membrane was visualized by fusing FhuA to red fluorescent protein (mRFP) (FIG. 16A). The *E. coli* FhuA-mRFP fusion was also expressed in *R. eutropha* under the control of the arabinose-inducible pBAD promoter[13]; the strain containing pBAD-mRFP plasmid was constructed as a control. *R. eutropha* cells expressing the FhuA-mRFP fusion exhibited fluorescent haloes, or brighter perimeters, indicating membrane localization (FIG. 16C). In contrast, expression of unfused cytoplasmic mRFP resulted in bright, uniform fluorescence throughout the cell (FIG. 16B). Visual comparison of *R. eutropha* and *E. coli* demonstrated that the FhuA-mRFP localization was similar in both strains (FIGS. 16A and 16C).

Figure 13:
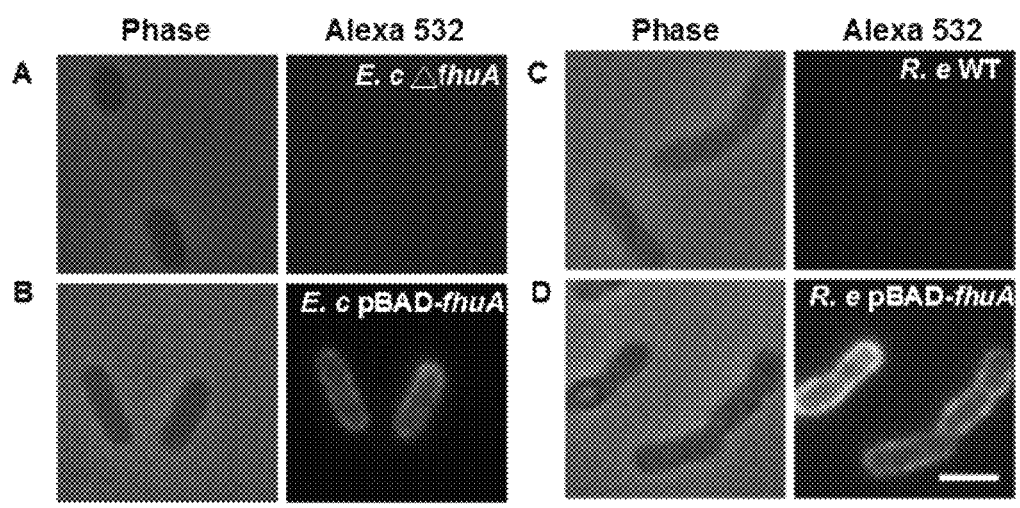
FIG. 13 shows immunolocalization of pb5-His treated cells. (A) E. coli ΔfhuA, (B) E. coli pBAD-FhuA, (C) wild-type R. eutropha (D) R. eutropha pBAD-FhuA. Cells were induced with 0.2% arabinose for 3 h. Next, 50 nM of purified His-pb5 proteins were incubated with cells for 15 min. The cells were then washed, immunolabeled with fluorescently conjugated anti-His antibodies (Alexa Fluor 532) for one hour, washed, and analyzed using fluorescence microscopy. Scale bar: 1 □m.

Bacteriophage T5 protein pb5 was expressed in *E. coli* with a 6×-His tag, purified, and incubated with live *E. coli* and *R. eutropha* cells expressing FhuA. The cells were immunolabeled with fluorescently conjugated anti-His antibodies (Alexa Fluor 532). Both *E. coli* and *R. eutropha* strains expressing FhuA showed extensive labeling on cell surfaces by fluorescence microscopy, consistent with the binding of pb5 to the cell surface (FIG. 13B). The specificity of the pb5-FhuA interaction was confirmed by absence of observable fluorescence after incubation of pb5 with an *E. coli* ΔfhuA strain[14] and wild-type *R. eutropha*. These controls confirmed the specificity of pb5 for FhuA on the bacterial cell surface (FIGS. 13C and 13D).

Figure 14:
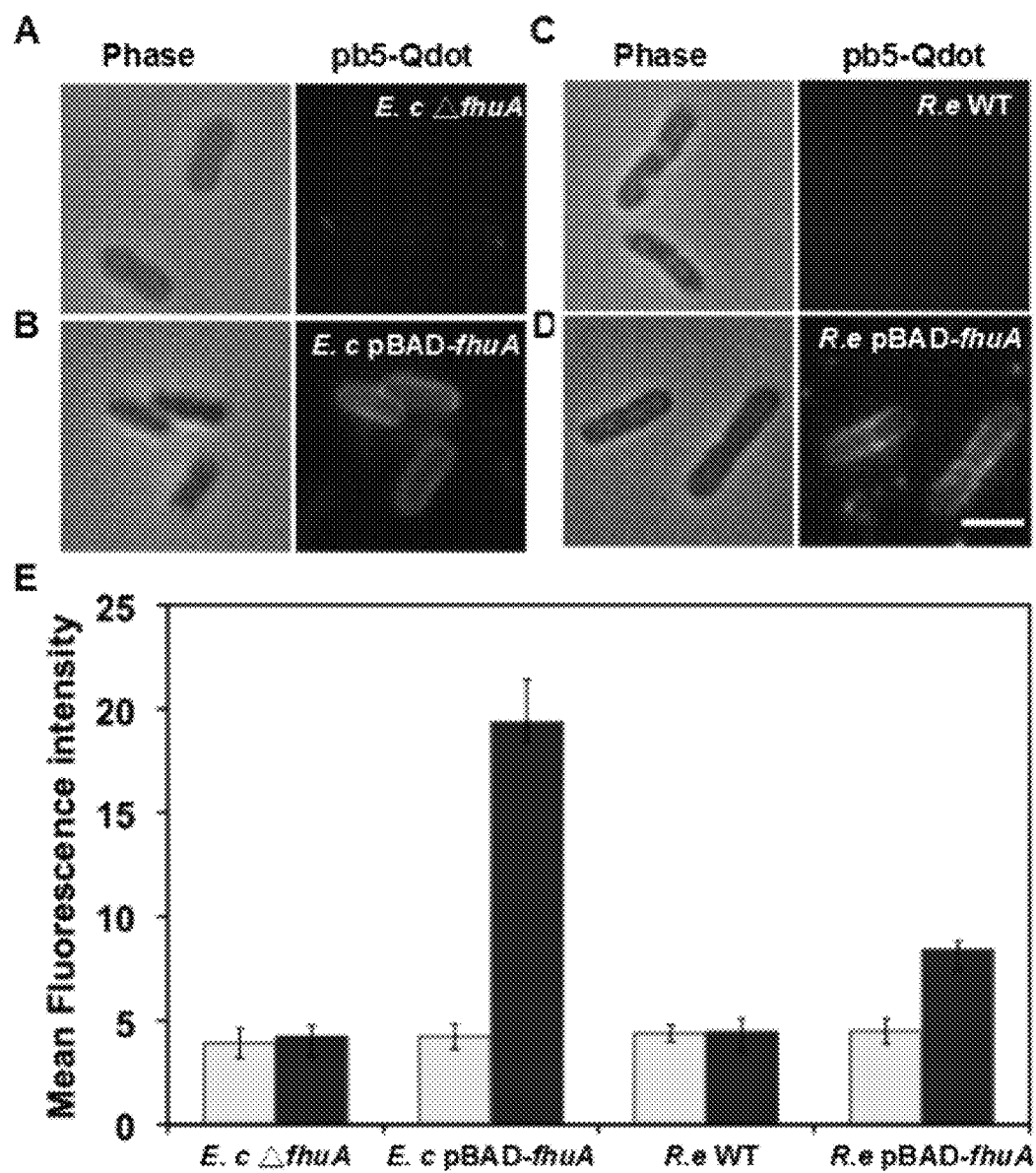
FIG. 14 shows selective labeling of FhuA targeted by Qdot-pb5. Fluorescence microscope images of (A) E. coli ΔfhuA, (B) E. coli pBAD-FhuA, (C) wild-type R. eutropha (D) R. eutropha pBAD-FhuA. Both E. coli and R. eutropha cells were treated with Qdot-pb5 in PBS. Qdot-pb5 was incubated with cells expressing FhuA for 15 min. The cells were then washed and analyzed using microscopy or flow cytometry (E). Scale bar: 1 □m. (E) Quantitative analysis of the targeting selectivity of Qdot-pb5. Light grey bars: in the absence of the inducer arabinose; dark grey bars: in the presence of the inducer. Error bars represent one standard deviation from three replicate experiments.
Figure 17:
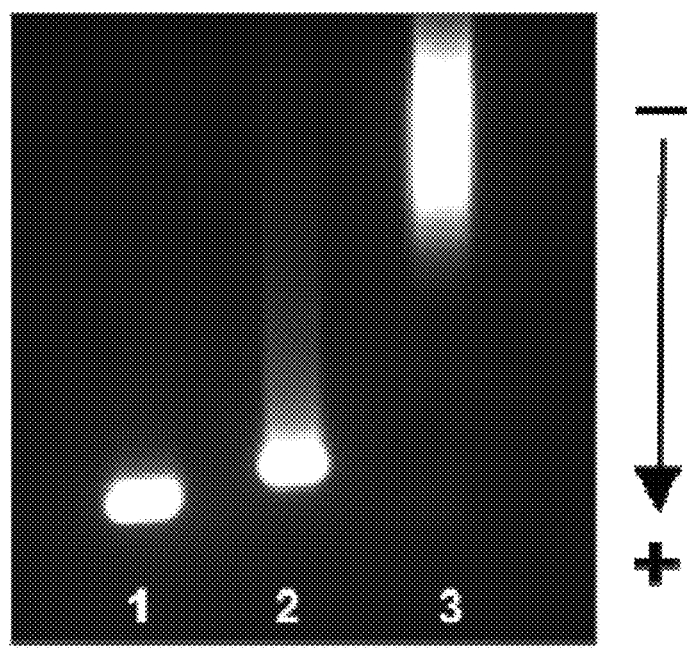
FIG. 17 shows agarose gel electrophoresis (separate conjugates with 0.5% agarose gel for 40 min at 100V in 0.5×TAE buffer) of pb5-conjugated Qdots. Lane 1: Qdot only. Lane 2: Qdot with EDC. Lane 3: purified Qdot-pb5.
Figure 18:
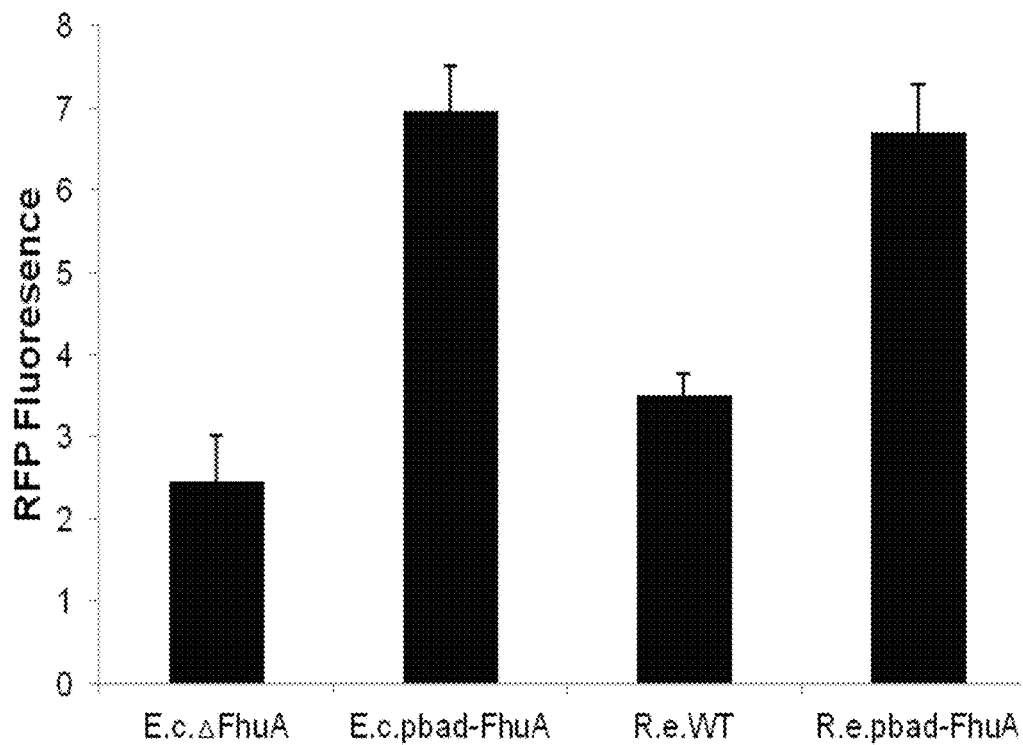
FIG. 18 shows flow cytometry analysis of RFP expression for E. coli and R. eutropha cells.
Figure 19:
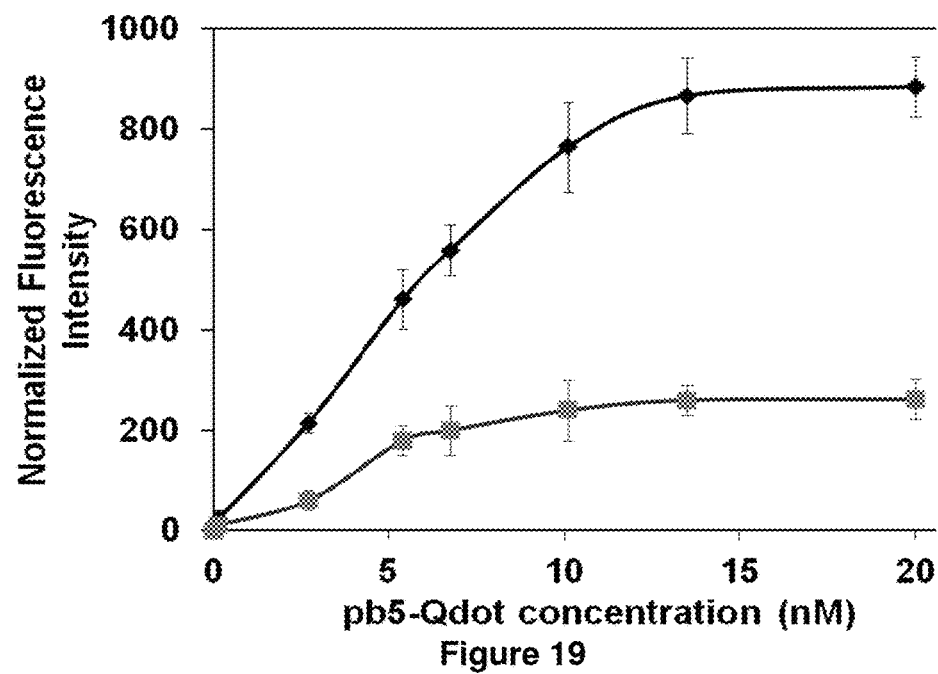
FIG. 19 shows quantitative analysis of the labeling affinity of Qdot-pb5 for E. coli (black diamonds) and R. eutropha (gray squares) cells by flow cytometry. After being incubated with Qdot-pb5 ranging from 2.5 to 20 nM, the cells were washed and analyzed. Error bars represent one standard deviation from three replicate experiments.

Controlled surface functionalization of *E. coli* and *R. eutropha* was performed by conjugating CdSe/ZnS quantum dots (Qdot) to pb5 using carbodiimide coupling chemistry and incubating the Qdot-pb5 conjugate with the bacterial cells[15]. The Qdot-protein coupling was confirmed by observation of decreased mobility on 0.5% agarose gels for the Qdot-pb5 conjugate compared to the free Qdot band and Qdot-carbodiimide mixtures (FIG. 17). Binding of Qdot-pb5 conjugate to *E. coli* and *R. eutropha* cells that expressed FhuA was demonstrated by the observation of fluorescence on the cell surface (FIG. 14). Visual comparison between the two strains revealed that *R. eutropha* had a weaker fluorescence signal compared to *E. coli* (FIGS. 14B and 14D). Binding of Qdot-pb5 conjugates to ΔfhuA *E. coli* and wild-type *R. eutropha* strains revealed minimal background fluorescence, demonstrating that the observed fluorescence was not due to non-specific Qdot aggregation (FIGS. 14A and 14C). Flow cytometry was employed to quantify the binding of Qdot-pb5 conjugates to FhuA on the surface of *E. coli* and *R. eutropha* (FIG. 14E). *E. coli* cells displayed ~3.4-fold higher binding efficiency to Qdot-pb5s compared to *R. eutropha* (FIG. 14E). The maximum number of the Qdots was estimated to be $5.1 \times 10^4$ (*E. coli*) and $1.5 \times 10^4$ (*R. eutropha*) molecules per cell. This result suggested that there were fewer FhuA molecules on the surface of *R. eutropha*. However, flow cytometry of the *E. coli* and *R. eutropha* cells expressing FhuA-mRFP demonstrated very similar amounts of FhuA on the cell surface of both strains (FIG. 18), suggesting that pb5 recognition of FhuA was dependent on its in vivo structure or the inherent properties of the *R. eutropha* outer membrane that may alter the FhuA-pb5 interaction. The dependence of labeling efficiency on the concentration of Qdot-pb5 was determined for the Qdot-pb5 to the bacterial surfaces. The FhuA-expressing *E. coli* cells were treated with Qdot-pb5 at concentrations ranging from 2.5 to 20 nM (FIG. 19). For both *E. coli* and *R. eutropha*, pb5 binding saturated at ~13.5 nM and the total binding was ~3.4 times lower for *R. eutropha*, which was consistent with single cell measurements.

Figure 15:
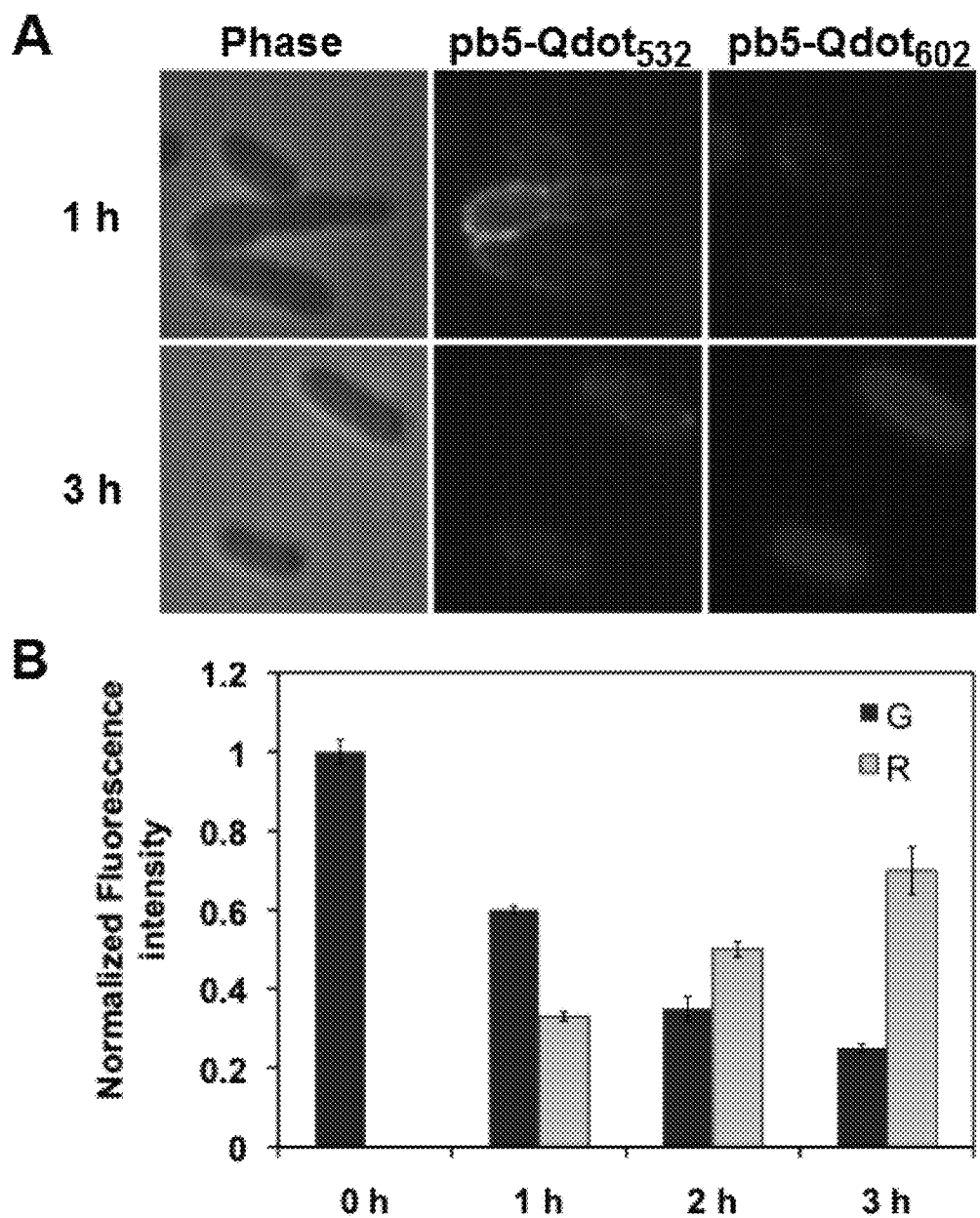
FIG. 15 shows pulse labeling of FhuA under conditions of continuous expression. E. coli cells expressing FhuA were labeled with Qdot532-pb5 first. Then, cells were withdrawn from cultures at indicated time point and labeled with Qdot602-pb5 for fluorescence microscopy (A) or flow cytometry (B). (A) Representative images of cells are shown with Qdot532-pb5 signals in green and Qdot602-pb5 in red. (B) Quantitative results are plotted as fold difference normalized against signals obtained after incubation with 20 nM Qdot532-pb5 or Qdot602-pb5 for 15 minutes.
Figure 20:
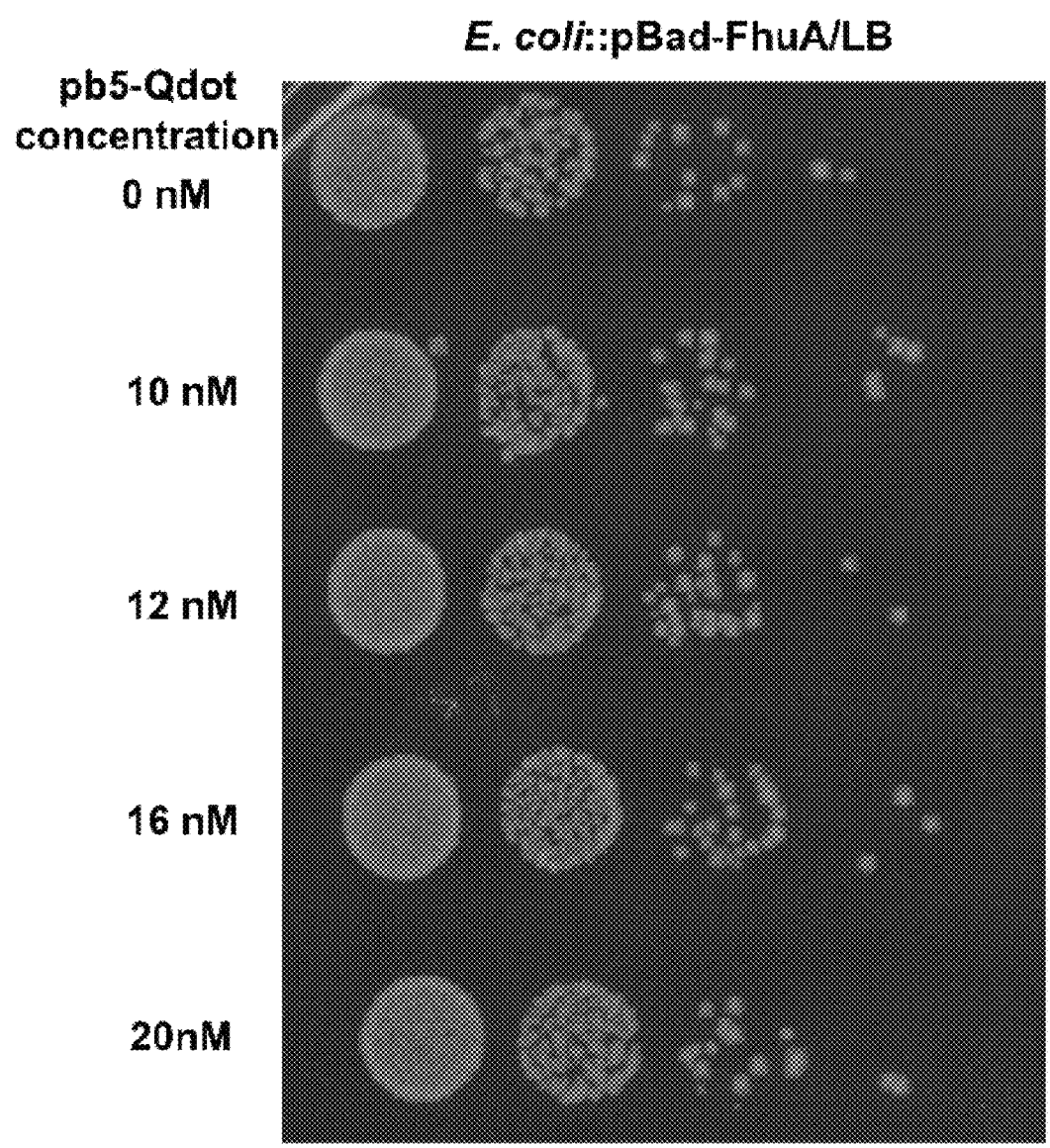
FIG. 20 shows growth of Qdot-pb5 treated cells (from left to right, ten-fold serial dilution of cells). Quantitative survival measurements in the presence of various concentrations of Qdot-pb5 are shown.

Pulse labeling with a second Qdot color established that cells treated with the Qdot-pb5 conjugates continued to divide and still bound pb5, demonstrating that it is an extremely stable complex in vivo as well as in vitro[7, 9] (FIG. 15A). FhuA-overexpressing and ΔfhuA *E. coli* cells were labeled with the Qdot532-pb5, and resuspended in LB media containing arabinose for 1, 2 or 3 h. Cells were withdrawn and treated with a Qdot602-pb5 to label the pool of newly expressed FhuA. Cells labeled with Qdot602-pb5 increased at every time point, consistent with the continued expression of FhuA (FIGS. 15A and 15B). However, the Qdot532-pb5 labeled cells persisted indicating that they were tightly bound to the cell surface. There was little or no labeling observed with either the first or second color probes in ΔfhuA cells. This result indicated that the binding of the Qdot-pb5 complex was not toxic to *E. coli* cells. To confirm this hypothesis, the number of colony forming unit (CFU) were evaluated after cells were treated with Qdot-pb5 and washed with PBS. The CFU assay confirmed that no significant change in toxicity occurred as Qdot-pb5 concentrations increased from 0-20 nM (FIG. 20).

In summary, we have established a novel method for functionalizing live bacterial cells using the interaction of a phage protein with its outer membrane receptor on the bacterial cell surface. The interaction was demonstrated in its native host, E. coli, and exported to R. eutropha, suggesting that the FhuA-pb5 interaction may be generalized to functionalize the surface of other gram-negative bacteria. Quantitative comparisons of the FhuA-pb5 interactions in E. coli and R. eutropha demonstrated that the interaction of FhuA-pb5 likely was different in the two strains and this interaction may be understood in the context of different structures of bacterial outer membranes.[16] The introduction of the FhuA-pb5 interaction into a foreign host also suggests that bacteriophage-receptor protein complexes may be a modular unit for surface functionalization. The protein complex between E. coli LamB and protein gpJ from bacteriophage λ the only other well-characterized bacteriophage-receptor protein complex, may offer a useful comparison to the FhuA-pb5 complex as a surface functionalization module.[17, 18] The discovery of new complexes, especially from bacteriophages that target bacteria besides E. coli, would broaden the scope of this method.

Materials and Methods

Bacterial Strains, Growth Conditions, and Cloning

E. coli and R. eutropha cells were cultured at 37° C. and 30° C. respectively in Luria-Bertani (LB) medium overnight in a shaker (200 rpm). Cells were then diluted (1:1000) in LB media supplemented with 0.2% arabinose. Strains and plasmids used are listed in Table 1. Standard protocols for conjugation with E. coli strain 517-1 were used to generate R. eutropha H16 strains (Brigham, C. J.; Budde, C. F.; Holder, J. W.; Zeng, Q. D.; Mahan, A. E.; Rha, C.; Sinskey, A. J. J. Bact. 2010, 192, 5454; hereby incorporated by reference). Cloning was performed in E. coli using standard procedures. E. coli strains (YC_008-009, YC_015) and R. eutropha strains (YC_012-014), and plasmids (pYC_006, pYC_008, pYC_009, pET29b-pb5) along with their associated information (annotated Genbank-format sequence files), have been deposited in the public instance of the JBEI Registry (https://public-registry.jbei.org; entries JPUB_000551-564) and are available from addgene (http://www.addgene.org).

Fluorescence Microscopy and Immunolocalization

Cells were immobilized using a thin layer of agarose in PBS medium. For localization studies, 0.2% arabinose was used to induce expression of fluorescent protein fusions from the araB promoters for at least 2 h. Differential interference contrast (DIC) and fluorescence microscopy images were obtained using a Leica DM 4000 B microscope with an HCX PL APO 100×, and oil PH3 CS objective.

For immunolocalization labeling, given strains were first washed with PBS once and mixed with pb5 for 15 minutes at room temperature. Cells were washed with PBS three times to remove unbound pb5 and fixed with 4% paraformaldehyde at 4° C. overnight. Cells were washed with PBS and blocked with Qiagen blocking reagent for 1 h. Samples were probed with α-penta-His-Alexa Fluor 488 conjugate at the (1:1000) concentration for 1 h prior to examine by microscopy.

Protein Purification and Immunolocalization

Protein pb5 was purified by metal chelate affinity chromatography using a HisPur nickel spin column as described previously.[9] Protein pb5 was then exchanged by chromatography on a PD10 Desalting column, with 10 mM sodium phosphate (pH 7.0). Then, pb5 (0.5 mg/mL) and Qdot were incubated at room temperature for 2 h.

Qdot-Pb5 Attachment

480 μL pb5 protein (0.5 mg/mL), 24 μL Qdot stock solution (8 μM), and 5.7 μL EDC (1 mg/mL) were added in 400 μL phosphate buffer solution (10 mm, pH 7.4) and incubated at room temperature for 2 h with gentle stirring. The Qdot-pb5 bioconjugate was separated from free pb5 protein and excess EDC by filtration through a 100 K filter unit for five times. The solution containing the Qdot-pb5 complex was mostly used immediately after synthesis or stored at 4° C. before flow cytometry or fluorescence microscopy.

Photoluminescence Analysis

Photoluminescence of cells was assessed on Guava easyCyte 8HT flow cytometer (Millipore, Billerica, Mass.), and the data were analyzed by using Guava Software (Guava Technologies, Hayward, Calif.). QD523 was diluted to indicate concentration in PBS for titration experiments. The concentrations of Qdot-pb5 were determined by intensity of photoluminescence relative to Qdot only. Control experiments were performed by adding Qdot in PBS. The measurement was performed on the Infinite F200P microplate reader (TECAN, Research Triangle Park, N.C.).

TABLE 1

Strains and plasmids

| Strain | Relevant genotype | Construction and source |
|---|---|---|
| E. coli S17-1 | recA pro hsdR RP4-2-Tc::Mu-Km::Tn7 | Transformation host |
| E. coli BW25113 | Δ(araD-araB)567, ΔlacZ4787(::rrnB-3), lambda⁻, rph-1, Δ(rhaD-rhaB)568, hsdR514 | Parental strain of Keio collection[14] |
| E. coli BL21 | F⁻ ompT gal dcm lon hsdSB ($r_B^-$ $m_B^-$) λ(DE3) | Protein production strain (Studier, F. W.; Moffatt, B. A. J. Mol. Biol. 1986, 189, 113; hereby incorporated by reference) |
| E. coli BW25113 ΔfhuA | Δ(araD-araB)567, ΔlacZ4787(::rrnB-3), lambda⁻, rph-1, Δ(rhaD-rhaB)568, hsdR514 ΔfhuA | fhuA deletion mutant of E.coli BW25113 (Keio collection)[14] |
| YC_008 | Δ(araD-araB)567, ΔlacZ4787(::rrnB-3), lambda⁻, rph-1, Δ(rhaD-rhaB)568, hsdR514 pBAD-fhuA-rfp | pYC_008 plasmid transformed into E. coli BW25113 |
| YC_009 | Δ(araD-araB)567, ΔlacZ4787(::rrnB-3), lambda⁻, rph-1, Δ(rhaD-rhaB)568, hsdR514 pBAD-fhuA | pYC_009 plasmid transformed into E. coli BW25113 |

TABLE 1-continued

Strains and plasmids

| Strain | Relevant genotype | Construction and source |
|---|---|---|
| R. eutropha H16 | Wild type | DSM 428 |
| YC_012 | R. eutropha pBAD-rfp | pYC_006 conjugated into R. eutropha H16 |
| YC_013 | R. eutropha pBAD-fhuA-rfp | pYC_008 conjugated into R. eutropha H16 |
| YC_014 | R. eutropha pBAD-fhuA | pYC_009 conjugated into R. eutropha H16 |
| YC_015 | E. coli BL21 pET29b-pb5 | pET29b-pb5 transformed into E. coli BL21 |

Table 2

Plasmids used in this study

| Plasmids | Relevant genotype | Source |
|---|---|---|
| pYC_006 | pBBRMCS plasmid with pBAD-rfp | this study |
| pYC_008 | pBBRMCS plasmid with pBAD-fhuA-rfp | this study |
| pYC_009 | pBBRMCS plasmid with pBAD-fhuA | this study |
| pET29b-pb5 plasmid | pET29b plasmid with pb5 | this study |

TABLE 3

Oligonucleotides used in this study

| Designation | Sequence |
|---|---|
| Pb5_NdeI_fw | TTTTcatatgAGCTTCTTCGCGGGCAAGCTGAACA (SEQ ID NO: 2) |
| Pb5 EcoRI rv | TTTTgaatccggGGTCAGGCGCTGGATGATCAGCTTGATGTTCG (SEQ ID NO: 3) |
| FhuA-RFP BglII fw | TTTTTagatcttttaagaaggagatataATGGCCCGCAGCAA (SEQ ID NO: 4) |
| FhuA-RFP NdeI rv | TTTTcatatgGAAGCGGAAGGTGGCGGTGG (SEQ ID NO: 5) |
| FhuA XhoI rv | TTTTctcgagtcaGAAGCGGAAGGTGGCGGTGG (SEQ ID NO: 6) |

REFERENCES CITED IN EXAMPLE 4

1. M. Boyce and C. R. Bertozzi, *Nat. Methods*, 2011, 8, 638-642.
2. J. A. Prescher and C. R. Bertozzi, *Nature Chemical Biology*, 2005, 1, 13-21.
3. J. A. Prescher, D. H. Dube and C. R. Bertozzi, *Nature*, 2004, 430, 873-877.
4. V. W. Cornish, K. M. Hahn and P. G. Schultz, *Journal of the American Chemical Society*, 1996, 118, 8150-8151.
5. A. J. Link and D. A. Tirrell, *Journal of the American Chemical Society*, 2003, 125, 11164-11165.
6. A. A. Twite, S. C. Hsiao, H. Onoe, R. A. Mathies and M. B. Francis, *Advanced Materials*, 2012, 24, 2380-2385.
7. A. Flayhan, F. Wien, M. Paternostre, P. Boulanger and C. Breyton, *Biochimie*, 2012, 94, 1982-1989.
8. M. Mondigler, R. T. Vogele and K. J. Heller, *Fems Microbiology Letters*, 1995, 130, 293-300.
9. L. Plancon, C. Janmot, M. le Maire, M. Desmadril, M. Bonhivers, L. Letellier and P. Boulanger, *J Mol Biol*, 2002, 318, 557-569.
10. H. Basit, K. S. Sharma, A. Van der Heyden, C. Gondran, C. Breyton, P. Dumy, F. M. Winnik and P. Labbe, *Chemical Communications*, 2012, 48, 6037-6039.
11. A. Pohlmann, W. F. Fricke, F. Reinecke, B. Kusian, H. Liesegang, R. Cramm, T. Eitinger, C. Ewering, M. Potter, E. Schwartz, A. Strittmatter, I. Voss, G. Gottschalk, A. Steinbuchel, B. Friedrich and B. Bowien, *Nature Biotechnology*, 2007, 25, 478-478.
12. H. Li, P. H. Opgenorth, D. G. Wernick, S. Rogers, T. Y. Wu, W. Higashide, P. Malati, Y. X. Huo, K. M. Cho and J. C. Liao, *Science*, 2012, 335, 1596-1596.
13. T. Fukui, K. Ohsawa, J. Mifune, I. Orita and S. Nakamura, *Applied Microbiology and Biotechnology*, 2011, 89, 1527-1536.
14. T. Baba, T. Ara, M. Hasegawa, Y. Takai, Y. Okumura, M. Baba, K. A. Datsenko, M. Tomita, B. L. Wanner and H. Mori, *Molecular Systems Biology*, 2006, 2.
15. D. E. Akin, W. H. Morrison, 3rd, L. L. Rigsby, F. E. Barton, 2nd, D. S. Himmelsbach and K. B. Hicks, *Appl Biochem Biotechnol*, 2006, 129-132, 104-116.
16. R. Koebnik, K. P. Locher and P. Van Gelder, *Molecular Microbiology*, 2000, 37, 239-253.
17. E. Berkane, F. Orlik, J. F. Stegmeier, A. Charbit, M. Winterhalter and R. Benz, *Biochemistry*, 2006, 45, 2708-2720.
18. J. R. Meyer, D. T. Dobias, J. S. Weitz, J. E. Barrick, R. T. Quick and R. E. Lenski, *Science*, 2012, 335, 428-432.

The above references are incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A host cell comprising: (a) a first membrane-bound protein or peptide bound directly or indirectly to an electrocatalyst molecule, (b) enzymes capable of synthesizing a biologically derived compound, and (c) optionally a second protein or peptide bound to the electrocatalyst molecule, wherein the first protein or peptide is bound to the second protein or peptide; wherein the host cell is *Escherichia coli* or of the genus *Ralstonia*, and the electrocatalyst molecule is a cobalt(II) complex supported by tetradentate polypyridyl ligand 2-bis(2-pyridyl)(methoxy)methyl-6-pyridylpyridine (PY4) or a CdSe/ZnS nanoparticle; wherein the biologically derived compound is an alkane, alcohol, fatty acid, ester, or isoprenoid.

2. The host cell of claim 1, further comprising one or more nucleic acids encoding genes for the first protein or peptide, enzymes for synthesizing a biologically derived compound, and optionally the second protein or peptide.

3. The host cell of claim 1, wherein the first and/or second protein or peptide is translocated to or outside of the outer membrane of the host cell upon expression within the host cell.

4. The host cell of claim 1, wherein the electrocatalyst molecule is a cobalt(II) complex supported by a CdSe/ZnS nanoparticle.

5. The host cell of claim 1, wherein the host cell is of the genus *Ralstonia*.

6. The host cell of claim 5, wherein the host cell is *R. basilensis, R. campinensis, R. eutropha, R. gilardii, R. insidiosa, R. mannitolilytica, R. metallidurans, R. paucula, R. pickettii, R. respiraculi, R. solanacearum, R. syzygii*, or *R. taiwanensis*.

7. The host cell of claim 6, wherein the host cell is *R. eutropha* H16.

8. The host cell of claim 1, wherein the first protein or peptide is *Escherichia coli* FhuA and the second protein or peptide is bacteriophage λ pb5.

9. The host cell of claim 1, wherein the host cell is capable of growing to a cell density of equal to or more than 200 g/L.

10. The host cell of claim 1, wherein the enzymes capable of synthesizing a biologically derived compound comprise: enzymes of an acyl-ACP reductase/aldehyde decarbonylase pathway, a thioesterase, enzymes of a mevalonate-dependent (MEV) isoprenoid pathway, enzymes of a deoxyxylulose 5-phosphate (DXP) pathway, an amophadiene synthase, a farnesene synthase, a bisabolene synthase, or a squalene synthase.

11. The host cell of claim 10, wherein the enzymes capable of synthesizing a biologically derived compound comprise a thioesterase, and the biologically derived compound is a fatty acid.

12. The host cell of claim 10, wherein the enzymes capable of synthesizing a biologically derived compound comprise enzymes of the acyl-ACP reductase/aldehyde decarbonylase pathway, and the biologically derived compound is an alkane.

13. The host cell of claim 10, wherein the enzymes capable of synthesizing a biologically derived compound comprise enzymes of the mevalonate-dependent (MEV) isoprenoid pathway, and the biologically derived compound is an isoprenoid.

14. The host cell of claim 10, wherein the enzymes capable of synthesizing a biologically derived compound comprise enzymes of the DXP pathway, and the biologically derived compound is an isoprenoid.

15. The host cell of claim 10, wherein the enzymes capable of synthesizing a biologically derived compound comprise an amophadiene synthase, farnesene synthase, bisabolene synthase, or squalene synthase, and the biologically derived compound is an amophadiene, farnesene, bisabolene, or squalene, respectively.

* * * * *

SEQUENCE LISTING

<160> NUMBER OF SEQ ID NOS: 6

<210> SEQ ID NO 1
<211> LENGTH: 6
<212> TYPE: PRT
<213> ORGANISM: Homo sapiens

<400> SEQUENCE: 1

Leu Cys Thr Pro Ser Arg
1               5

<210> SEQ ID NO 2
<211> LENGTH: 35
<212> TYPE: DNA
<213> ORGANISM: Escherichia coli

<400> SEQUENCE: 2
ttttcatatg agcttcttcg cgggcaagct gaaca                              35

<210> SEQ ID NO 3
<211> LENGTH: 44
<212> TYPE: DNA
<213> ORGANISM: Escherichia coli

<400> SEQUENCE: 3
ttttgaatcc ggggtcaggc gctggatgat cagcttgatg ttcg                    44

<210> SEQ ID NO 4
<211> LENGTH: 42
<212> TYPE: DNA
<213> ORGANISM: Escherichia coli

<400> SEQUENCE: 4
tttttagatc ttttaagaag gagatataat ggcccgcagc aa                      42

<210> SEQ ID NO 5
<211> LENGTH: 30
<212> TYPE: DNA
<213> ORGANISM: Escherichia coli

<400> SEQUENCE: 5
ttttcatatg gaagcggaag gtggcggtgg                                    30

<210> SEQ ID NO 6
<211> LENGTH: 33
<212> TYPE: DNA
<213> ORGANISM: Escherichia coli

<400> SEQUENCE: 6
ttttctcgag tcagaagcgg aaggtggcgg tgg                                33